United States Patent [19]

Sharpless et al.

[11] Patent Number: 5,321,143

[45] Date of Patent: Jun. 14, 1994

[54] RUTHENIUM-CATALYZED PRODUCTION OF CYCLIC SULFATES

[75] Inventors: K. Barry Sharpless, LaJolla, Calif.; Yun Gao, Framingham, Mass.

[73] Assignee: Massachusetts Institute of Technology, Cambridge, Mass.

[21] Appl. No.: 712,199

[22] Filed: Jun. 7, 1991

Related U.S. Application Data

[63] Continuation-in-part of Ser. No. 369,189, Jun. 21, 1989, Pat. No. 5,112,990, which is a continuation-in-part of Ser. No. 199,157, May 26, 1988, Pat. No. 5,023,342.

[51] Int. Cl.$^5$ ............................................. C07D 89/08
[52] U.S. Cl. ........................................................ 549/34
[58] Field of Search ......................................... 549/34

[56] References Cited

U.S. PATENT DOCUMENTS 3,454,597  7/1969  Tong et al. ............................ 549/34

FOREIGN PATENT DOCUMENTS 1049870  2/1959  Fed. Rep. of Germany .

OTHER PUBLICATIONS

G. Lowe and S. J. Salamone, *J. Chem. Soc., Chem. Commun.*, 1392–1394 (1983).
G. Lowe and S. J. Salamone, *J. Chem. Soc., Chem. Commun.*, 466–467 (1984).
D. Seebach, In: *Modern Synthetic Methods 1980*, 1:115–171 (1980).
S. Saito et al., *Tetrahedron Letters*, 27(43):5249–5252 (1986).
T. G. Hansson and J. O. Kihlberg, *J. Org. Chem.*, 51:4490–4492 (1986).
E. Hungerbuhler et al., *Angew. Chem. Int.* (Engl. Ed.) 18(12): 958–960 (1979).
M. J. Miller et al., *J. Org. Chem.*, 47: 4928–4933 (1982).
J. S. Bajwa and M. J. Miller, *J. Org. Chem.*, 48:1114–1116 (1983).
P. Schnurrenberger et al., *Liebigs Ann. Chem.*, 733–744 (1987).
S. Saito et al., *Tetrahedron Letters*, 26(43):5309–5312 (1985).
K. Mori and H. Iwasawa, *Tetrahedron*, 36: 87–90 (1980).
S. J. Brandes and J. A. Katzenellenbogen, *Molecular Pharmacology*, 32: 391–403 (1987).
Chem. Abst. 106 (13), p. 648, abst. #102179q (Mar. 30, 1987).
Chem. Abst. 105(25), p. 780, abst. #226452z (Dec. 22, 1986).
Chem. Abst. 86(23), p. 490, abst. #170716f (Jun. 6, 1977).
Chem. Abst. 101(15), p. 67, abst. #130322w (Oct. 8, 1984).
Shaik, *J. Am. Chem. Soc.* 105, 4359–4367 (1983).
Bordwell et al., *J. Am. Chem. Soc.* 86, 4645–4650 (1964).
Chem. Abst. 108, abst. #37493n (1988).
Breslow et al., Multi-Sulfur and Sulfur and Oxygen Five- and Six-Membered Heterocycles, pp. 1, 633 and 639 (1966).
Carlsen et al. *J. Org. Chem.* 46, 3936–3938 (1981).
Gao et al., *J. Am. Chem. Soc.* 110(22), 7538–7539 (1988).

*Primary Examiner*—Marianne M. Cintins
*Assistant Examiner*—Catherine S. Kilby Scalzo
*Attorney, Agent, or Firm*—Hamilton, Brook, Smith & Reynolds

[57] ABSTRACT

A ruthenium catalyzed method to synthesize cyclic sulfate compounds from the corresponding cyclic sulfites, and the cyclic sulfate reaction products obtained by this method. These cyclic sulfates further react with selected nucleophiles to give various substituted products. The method is an efficient means for the synthesis of chiral building blocks from tartaric acid enantiomers in high yields using an overall two-stage, one-pot reaction procedure. The chiral compounds can be transformed by nucleophilic reactions into chiral building blocks useful for the synthesis of natural biologically active products, such as antibiotics and pheromones.

7 Claims, No Drawings

RUTHENIUM-CATALYZED PRODUCTION OF CYCLIC SULFATES

RELATED APPLICATIONS

This application is a continuation-in-part of U.S. application Ser. No. 07/369,189, filed Jun. 21, 1989, now U.S. Pat. No. 5,112,990 issued May 12, 1992 which, in turn is a continuation-in-part of U.S. application Ser. No. 07/199,157 filed May 26, 1988 now U.S. Pat. No. 5,023,342 issued Jun. 11, 1991.

BACKGROUND OF THE INVENTION

The study of the relationship of three dimensional structure of organic or inorganic molecules is called stereochemistry, one aspect of which is the study of stereoisomers. Isomers are compounds which have the same molecular formula; stereoisomers differ from each other only in the way the atoms are oriented in space. Enantiomers are stereoisomers which are mirror images of each other and which share all of the same physical properties except one: the direction in which they rotate a plane polarized light, or optical rotation. Enanttomers are distinguishable from each other only by their optical rotation. Enantiomers display a property known as chirality. One characteristic of chiral molecules is that they are not superimposible on their mirror images. One enantiomer rotates the plane of polarized light to the left and the other enantiomer, its mirror image, rotates the plane of light to the right. If the rotation of the plane is to the right (clockwise), the substance is dextrorotatory, and the enantiomer is designated with a plus (+) sign. Conversely, if the optical rotation is to the left (counterclockwise), the substance is levorotatary, and the enantiomer is designated as minus (−). Enantiomers display equal, but opposite, optical rotation.

The existence of stereotsomers provides us with one of the most sensitive probes into mechanisms of chemical and biological reactions. Despite the very close similarity of enantiomers, they may display very different properties in chemical and biological reactions or transformations, Although very similar in structure, one isomer of the chiral pair may serve as an antibiotic, heart stimulant, food, or display other biological activity, and the other isomer may be totally biologically inert or has the opposite and toxic effect. J. March, *Advanced Organic Chemistry*, page 87, (2nd edition) McGraw Hill Co., New York, N.Y. (1977).

Enantiomers have identical chemical properties, except their interactions with optically active reagents. Enantiomeric molecules undergo the same chemical reactions with achiral molecules, and at the same rates, since the atoms of each are influenced in their reactivity by exactly the same combination of substituents. A reagent approaching either enantiomer encounters the same environment, except that one environment is the mirror image of the other. In the case of an optically active reagent, however, the influences exerted on the reagent in its attack on the enantiomers are not identical, and reaction rates will be different. In some systems of this nature, the reaction will not take place at all for one of the isomers.

In biological systems, such stereospecificity is the rule rather than the exception. The most obvious reason for this is that enzymes and most of their targets are optically active molecules. For example, (+)-glucose is an extremely important metabolite, but (−)-glucose is biologically inactive. The hormonal activity of (−)-adrenaline is several times greater than its mirror image (+)-adrenaline, and only one enantiomer of the compound chloromycetin is an antibiotic. (For other examples see R. T. Morrison and R. N. Boyd, *Organic Chemistry*, 3rd edition, Allyn and Bacon, Inc., Boston, Mass. pages 126-127) This stereospecific activity is one reason why chiral molecules are so important as a basis for bioactive compounds.

Tartaric acid, ($C_4H_6O_6$) which is readily available in both enantiomeric forms, is an extremely useful and versatile chiral starting material for natural product and drug synthesis. Tartaric acid is used extensively in industry and as a food acidulant. Its two-fold symmetry axis causes all four functionalized carbon atoms to exist as homotopic pairs and thus simplifies its functional group transformations. Owing to its unique properties, many synthetic applications based on tartaric acid have been developed. For example, D. Seebach and coworkers describe the synthesis of chiral compounds from tartartic acid enantiomers in *Modern Synthetic Methods* 1980, R. Scheffold (ed.), Otto Salle Verlag, Frankfurt, FRG, p. 115-171 (1980). Hungerbuhler et al. describe the synthesis of chiral agents from tartaric acid using an epoxyalcohol intermediate in *Angew. Chem. Int. Ed. Engl.*, 18(12):958-960 (1979). Schnurrenberger, et al. describe the synthesis of a chiral antibiotic, (+)-colletodiol, in *Liebigs. Ann. Chem.*, pages 733-744 (1987). Mori and Iwasawa describe the synthesis of chiral pheromones using the enantiomers of tartrate as starting materials in *Tetrahedron*, 36:87-90(1980). Saito et al. describe the production of four stereoisomers of pure 2, 3-epoxyesters from tartaric acids in *Tetrahedron Letters*, 27(43)(:5249-5252 (1986). Hansson and Kihlberg describe the synthes is of an optically active derivative of the amino acid aspartic acid in *J. Org. Chem.*, 51:4490-4492 (1986).

Other cyclic systems are described by Guiller, A. et al. in *Tetrahedron Lett.* 1985, p. 6343; Tewson, T. J. and M. J. Welch in *J. Nucl. Med.*, 21:559 (1980); David, S. and S. Hanessian, *Tetrahedron*, 41:643 (1985); Ricci, A. et al. in *J. Chem. Soc. Chem. Commun.*, p. 1458 (1985); and Shanzer, A., *Tetrahedron Lett.* 1980, p. 221 (1980).

SUMMARY OF THE INVENTION

The present invention relates to ruthenium-catalyzed conversion of cyclic sulfites to cyclic sulfates, methods of producing cyclic sulfates by ruthenium-catalyzed in situ oxidation of cyclic sulfites, compounds produced by such methods and methods of reacting the resulting cyclic sulfates with selected nucleophiles. More particularly, the invention relates to tartrate cyclic sulfate compounds, particularly tartrate cyclic sulfate diesters and diamtdes, and to a method of producing such compounds. In the method of the present invention, tartrate cyclic sulfate compounds are synthesized from dialkyl tartrates in a two-stage reaction in which the tartrates are cyclized to form the corresponding cyclic sulfite, which are then converted to the corresponding cyclic sulfate by ruthenium-catalyzed in sttu oxidation of the cyclic sulfites. Ruthenium-catalyzed in situ oxidation of cyclic sulfites produced or obtained by other means can also be carried out by the method of the present invention.

The invention further relates to products produced by reacting the cyclic sulfate compounds with selected nucleophiles, to produce substituted products useful for natural product and drug syntheses, as well as to a method of producing such compounds. The present method provides an efficient means of synthesizing chiral building blocks from tartrates or other compounds using a two stage, one-pot procedure which produces high yields of the desired product.

The method of the invention produces cyclic sulfate compounds having the general structure:

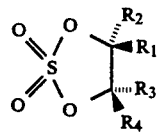

and its enantiomers, wherein $R_1$, $R_2$, $R_3$ and $R_4$ can be any organic or inorganic substituent which forms a covalent bond with a carbon atom of the starting compound, and which permits formation of the stable, sulfite and sulfate ring structures. $R_1$, $R_2$, $R_3$ and $R_4$ can be hydrogen, alkyl, aryl (e.g., phenyl, benzyl, phenoxy, benzyloxy benzylamide groups), carbonyl (e.g., aldehydes or ketones), carboxylic esters, carboxyalkyl, amide or any other organic group, providing that the corresponding cyclic sulfite and cyclic sulfate ring structures are stable, and that $R_1$-$R_4$ are stable under the reaction conditions (i.e., they do not decompose or become oxidized during the reaction). For example, when $R_1$, $R_2$, $R_3$ and $R_4$ hydrogen, alkyl or aryl groups, the above structure represents a simple 1,2 cyclic sulfate. When either $R_1$ or $R_2$ is an ester group and the other is hydrogen, and either $R_3$ or $R_4$ is an alkyl group and the other is hydrogen, the structure represents an $\alpha,\beta$ unsaturated-ester cyclic sulfate. When either $R_1$ or $R_2$ is an amide group and the other is hydrogen, and either $R_3$ or $R_4$ is an alkyl group and the other is hydrogen, the structure represents an $\alpha,\beta$-amide cyclic sulfate. When either $R_1$ or $R_2$ is an ester group and the other is hydrogen and either $R_3$ or $R_4$ is also an ester group and the other hydrogen, the structure represents a tartrate 2,3 cyclic sulfate. All four R groups may be different.

The method of the invention produces tartrate cyclic sulfate diesters having the general structure:

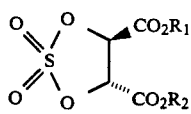

and its enantiomers. $R_1$ and $R_2$ can be alkyl or aryl (e.g., aromatic substituent) groups. $R_1$ and $R_2$ are generally the same, although they may be different. $R_1$ or $R_2$, but not both, can be hydrogen.

The method of the invention also produces tartrate cyclic sulfate diamides having the general structure:

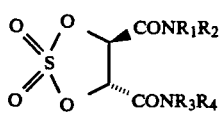

and its enantiomers, wherein $R_1$, $R_2$, $R_3$ and $R_4$ can be hydrogen, or an alkyl or aryl (e.g., phenyl, benzyl, phenoxy, benzyloxy, benzylamide) group. Each of the four substituents can be different. $R_1$ and $R_3$ will generally be the same, although they may be different. Similarly, $R_2$ and $R_4$ will generally be the same, but they may also be different. All four substituents may be the same, except in the case of hydrogen; at least one substituent must be other than hydrogen.

The process of the present invention is used to produce both enantiomers of cyclic sulfate compounds. For example, tartrate cyclic sulfate diesters and tartrate cyclic sulfate can be produced from either (+)-tartrate esters or amides, respectively, or (−)-tartrate esters or amides, respectively. These cyclic tartrate diesters and diamides are then transformed by nucleophilic reactions into chiral building blocks which can be used as chiral synthons for natural product and drug syntheses.

DETAILED DESCRIPTION OF THE INVENTION

The present invention relates to the rutheniumcatalyzed conversion of cyclic sulfites to cyclic sulfates, methods of producing cyclic sulfates by ruthenium catalyzed in situ oxidation of the cyclic sulfites, compounds produced by such methods and methods of reacting the cyclic sulfate products with a selected nucleophile. More particularly, the invention concerns tartrate cyclic sulfate diesters and diamides, and to methods of preparing them from dialkyl tartrates or dialkyl tartramides using a two-stage reaction process. The present process utilizes ruthenium-catalyzed oxidation of the corresponding cyclic sulfites. The tartrate cyclic sulfate diesters and diamides are chiral compounds which can be used to produce biologically active substances, such as antibiotics and pheromones. The invention further relates to the reaction of these chiral compounds with nucleophiles to form various substituted chiral compounds useful for the production of drugs, and other biologically active products.

The method of the invention produces cyclic sulfate compounds having the general structure:

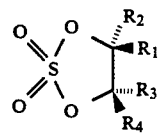

$R_1$, $R_2$, $R_3$ and $R_4$ can be any organic or inorganic group which forms a covalent bond with the carbon atoms of the starting compound, and which permits formation of the stable intermediate sulfite or sulfate ring structures. $R_1$, $R_2$, $R_3$ and $R_4$ can be hydrogen, aryl (e.g., phenyl, benzyl, phenoxy, benzyloxy, benzylamide), or alkyl groups such as methyl groups, ethyl groups, cyclohexyl groups, carbonyl (e.g., aldehydes or ketones) or carboxyalkyl groups, amides or any other group, providing that the sulfite and sulfate ring structures are stable and $R_1$-$R_4$ are stable under the reaction conditions. For example, it is unlikely that $R_1$ and $R_2$ can both be electron rich aromatic systems because the cyclic sulfate products will not be stable due to decomposition of the cyclic sulfate caused by the formation of benzylic type carbonium ions. Within the limitations set out above, $R_1$ through $R_4$ can be selected from a variety of substituent groups. All four R groups may be the same or different, however, all four R groups cannot be hydrogen. The general structure above shows one enantiomer. The other enantiomer can also be produced using the method of the present invention.

In one embodiment of the present invention, ruthenium-catalyzed oxidation is used to produce tartrate cyclic sulfates. Many synthetic transformations based on tartaric acid have been developed. However, an efficient general method of selective activation of one of the hydroxyl groups for substitution by carbon, hydrogen or other heteroatom nucleophiles (e.g., compounds including oxygen, nitrogen, sulphur and halides) has, until the present invention, been unavailable. According to the method of the present invention, dihydroxy cyclic sulfates are prepared by ruthenium-catalyzed oxidation of the corresponding cyclic sulfites with an oxidant such as, for example, sodium periodate (NaIO₄) or sodium hypochlorite (NaOCl), from vicinal dihydroxy tartrate compounds. These dihydroxy compounds may also be referred to herein as tartrate diols. The tartrate cyclic sulfate compounds produced by the present method can then be reacted with various nucleophiles followed by hydrolysis, to form a variety of useful chiral compounds. G. W. Fisher, et al., *Comprehensive Heterocyclic Chemistry*, vol. 6, Pergamon Press, Oxford, P. 851 (1984) and T. J. Tewson, *J. Org. Chem.*, 48:3507 (1983).

This method takes advantage of the C₂ symmetry of tartaric acid by simultaneously activating one hydroxyl group, and protecting the other hydroxyl group on the tartrate molecule via the cyclic intermediate.

Other starting materials may be used in addition to tartrates. For example, other 1,2 and 1,3 diols can be used as well as 1,2 and 1,3 aminoalcohols. The use of vicinal aminoalcohols will produce the intermediate cyclic sulfamite, which then undergoes ruthenium catalyzed oxidation, as described herein, to form the cyclic sulfamate. Using this process, cyclic sulfamates, such as ephedrine and pseudoephedrine cyclic sulfamate may be synthesized.

The 1,2-cyclic sulfate functionality was chosen because of its ease of access, thermostability and high reactivity toward nucleophiles (partly due to the ring strain inherent in the 5-membered sulfate ring structure). J. G. Tillett, *Phosphorus and Sulfur*, 341 (1976). The reactivity of tartrate cyclic sulfates is further enhanced by the carboxylate or amide groups present in the molecule. F. G. Bordwell and W. T. Brannen, Jr., *J. Am. Chem. Soc.* 86:4645 (1964); and S. S. Shaik, *J. Am. Chem. Soc.*, 105:4359 (1983).

Tartrate cyclic sulfate compounds are very stable at room temperature and under weakly acidic conditions, and show little moisture sensitivity. They react with various nucleophiles to form substituted mono-sulfate salts. These mono-substituted salts are much less reactive toward further nucleophile substitution, however. They hydrolyze under mild hydrolysis conditions in situ, through fission of the oxygen-sulfur bond to yield the β-substituted erythro malate esters. Surprisingly rapid hydrolysis occurs in the presence of acid sensitive groups. The reduced reactivity of the molecule after the first nucleophilic substitution indicates that the cyclic sulfate group functions as an activating group for one hydroxyl group, and at the same time, as a protecting group for the other hydroxyl group.

FIG. 1 illustrates the general reaction scheme of the present invention. It shows the production of tartrate cyclic sulfate diesters, including the starting and intermediate materials and the resulting tartrate cyclic sulfate diester products. The tartrate diester has the general formula:

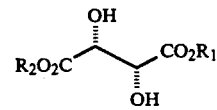

and is shown as compound (1) in FIG. 1. In this reaction scheme, R₁ and R₂ can be any alkyl or aryl group capable of forming ester linkages with tartaric acid. R₁ or R₂, but not both, can be hydrogen. For example, R₁ and R₂ can be methyl, ethyl, isopropyl or cyclohexyl groups. In a given tartrate starting compound and, thus, in the resulting products, R₁ and R₂ can be both the same, or can be different.

In addition, the starting materials can be diamides, which form a cyclic sulfate structure having the general formula:

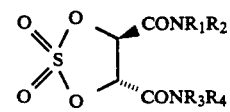

and its enantiomer. In this case, R₁, R₂, R₃ and R₄ can be hydrogen or any alkyl or aryl group capable of forming amide linkages with tartrate, and of forming stable cyclic sulfite intermediates and cyclic sulfate products. Mixed ester-amide starting materials can also be used, i.e., where one of the amide groups on the above structure is an ester group.

According to the method of the present invention, the starting material (e.g., a selected dihydroxy tartrate diamide or diester), is treated with a thionyl halide, such as thionyl chloride (SOCl₂), in an organic solvent, such as carbon tetrachloride (CCl₄), at an appropriate temperature (e.g., approximately 60° C.), to yield a cyclic sulfite compound. In most cases, there is no need for isolation of the sulfite; however, isolation may sometimes be preferable. In general, in the same reactor, the cyclic sulfite compound produced by the first stage of the reaction is combined with an oxidizing agent, which will generally be an inorganic compound such as sodium periodate (NaIO₄), sodium hypochlorite (NaOCl), sodium bromate (NaBrO₃), calcium hypochlortde (Ca(ClO)₂), sodium chlorate (NaClO₃) or oxone (HOODSO−). A catalytic quantity of a ruthenium-containing compound, such as ruthentum chloride (RuCl₃.3H₂O) or ruthenium oxide (RuO₂.(H₂O)ₓ is added, generally in combination with a solvent or solvent mixture such as acetonitrile (CH₃CN) and water. The ruthenium compounds which are useful are ruthenium salts capable of being oxidized to form ruthenium tetroxide. The mixture is stirred at room temperature until the reaction is complete. The product of the reaction is the tartrate cyclic sulfate. In this step, the intermediate cyclic sulfite is oxidized to produce the desired tartrate cyclic sulfate compound, which will have one of the two following general structures:

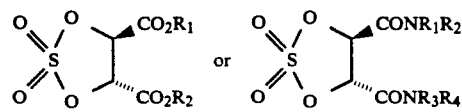

The preferred oxidant is sodium periodate, in an amount between about 1.0 to 1.5 equivalents to the substrate.

The preferred ruthenium catalyst is ruthenium (III) chloride. Preferred levels of the ruthenium chloride catalyst are between about 0.001 and 0.01 equivalents.

Diols containing acid-sensitive functionalities, such as acetonide and silyloxy groups, are efficiently converted to the corresponding cyclic sulfates by the present method. Reactions of these cylic sulfates with nucleophiles, such as sodium azide or benzoate, provides sulfates which can be hydrolyzed under mild acidic conditions. In this method, for example, a diol containing acid-sensitive functionalities, 1,3:5,6-di-O-isopropylidene-D-mannitol was treated with thionyl chloride in the presence of triethylamine. Almost quantitative formation of the corresponding cyclic sulfite occurred. Treatment of the crude reaction mixture under the usual catalytic oxidation conditions did not provide the corresponding cyclic sulfate, presumably due to inactivation of the ruthenium catalyst by the amine. However when the cyclic sulfite was isolated and then oxidized with catalytic $RuO_4$, it was converted to the cyclic sulfate in excellent yield (94% from the diol). Similarly, 3-t-butyldimethylsilyloxy-1,2-propanediol and ketal diol were smoothly converted to the corresponding cyclic sulfates in 87% and 95% yield, respectively.

Ruthenium-catalyzed oxidation of cyclic sulfite compounds to form the corresponding cyclic sulfate compounds can also be used with starting compounds other than tartrate dihydroxy diesters and diamides. For example, the method of the present invention can be used to cyclize other dihydroxy compounds, such as monoesters, monoamides, monocarboxylic acids and other carboxylate and non-carboxylate substituents. As mentioned above, non-dihydroxy compounds such as 1,3-aminoalcohols can also be used. Homochiral amtnoalcohols are key intermediates in the synthesis of many pharmaceuticals. In this case, one of the oxygen molecules in the ring structure will be replaced with a nitrogen molecule to form the cyclic sulfamate. Various cyclic sulfate compounds synthesized using the present method are shown in Table 1.

TABLE 1

One-pot Synthesis of Cyclic Sulfates[a]

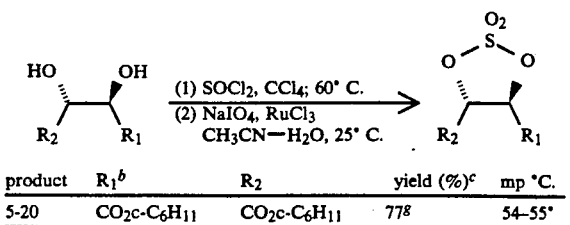

| product | $R_1$[b] | $R_2$ | yield (%)[c] | mp °C. |
|---|---|---|---|---|
| from simple dihydroxy compound | | | | |
| 5-5 | H | n-$C_8H_{17}$ | 92 | |
| 5-9 | H | c-$C_6H_{11}$(R) | 97[d] | 76° |
| 5-10 | $CH_3$(R) | $CH_3$(R) | 89[d] | |
| 5-11 | n-$C_4H_9$ | n-$C_4H_9$ | 89[11] | |
| 5-12 | Ph(R) | Ph(R) | 75[d] | 85° |
| from α,β-dihydroxy acid derivatives | | | | |
| 5-13 | $CO_2$c-$C_6H_{11}$ | H | 88 | 55-57° |
| 5-14 | $CO_2$Me | n-$C_{15}H_{31}$ | 90-95 | 45-46° |
| 5-15 | $CO_2$Et | c-$C_6H_{11}$ | 95-97 | |
| 5-16 | $CONHCH_2$Ph | H | 64 | 95-97° |
| from dialkyl tartrate[e] | | | | |
| 5-17 | $CO_2$Me | $CO_2$Me | 63[f] | 70-71° |
| 5-18 | $CO_2$Et | $CO_2$Et | 69[f] | 75-76° |
| 5-19a | $CO_2$i-Pr | $CO_2$i-Pr | 90-93 | |
| 5-19b | $CO_2$i-Pr | $CO_2$i-Pr | 71[g] | |
| 5-20 | $CO_2$c-$C_6H_{11}$ | $CO_2$c-$C_6H_{11}$ | 77[g] | 54-55° |

[a]Reactions were performed as described in the general procedure, except as noted.
[b]Letter in parenthesis is the absolute configuration of the carbon bearing the substituent.
[c]Yields are isolated yields.
[d]Prepared by Dr. B. B. Lohray.
[e](2R,3R)-(+)-tartrate were used except entry 13 which employed (−)-tartrate.
[f]Water was the last component added in the reaction.
[g]Yield was not optimized.

The resulting cyclic sulfate compounds can then be isolated and subsequently reacted with a selected nucleophile, such as sodium azide or ammonium thiocyanate. The isolation step is preferred but not necessary; the reaction with the nucleophile may be performed in situ. The general reaction scheme is shown in FIG. 2. Other nucleophiles are represented in Table 5 (below). These reactions are generally fast and proceed at room temperature or below in polar solvents under neutral, basic and acidic conditions.

Nucleophilic reagents, often referred to as nucleophiles, are substances that are electron-rich and can offer a pair of electrons for bond formation. Nucleophilic substitution is the displacement of one leaving group by a nucleophilic center in a chemical compound. Nucleophilic substitution can proceed by two different mechanisms: first-order kinetics, in which the reaction rate depends on the concentration of only one substance; and second-order kinetics, in which the rate depends upon the concentrations of two reactants. Chiral compounds which undergo second order reactions usually yield a product with inversion of configuration at the reaction site. The production of an optically pure product is critical because of the selectivity of biological systems for a particular enantiomer.

Cyclic sulfates are opened by most nucleophiles under mild conditions in dipolar aprotic solvents. Thus, chemoselective manipulation of compounds containing cyclic sulfate groups is possible.

The reaction of a cyclic sulfate compound and a selected nucleophile is described in Example 17 below and, in general, is carried out as described below. These substitutions proceed via second order kinetics to give a e-substituted β-succinate monosulfates, which are hydrolyzed under acidic conditions through fission of the O-S bond to yield the erythro-β-substituted malic esters. In general, the reaction is carried out as described below with specific reference to a tartrate diester: The tartrate cyclic sulfate diester formed as described above and represented by formula (1) below, is combined with a selected nucleophile. For example, it is combined with the nucleophile sodium azide ($NaN_3$), in a solvent or solvent mixture in which both the tartrate compound and the nucleophile are soluble (e.g., acetone/water mixture) and maintained for a sufficient time and at an appropriate temperature for reaction of the tartrate cyclic sulfate diester and the nucleophile to occur. The product is a compound of the general formula (2), wherein Nu represents the nucleophile.

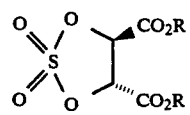
(1)

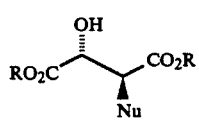
(2)

In particular, chiral diester compounds of one of the following formulae can be produced:

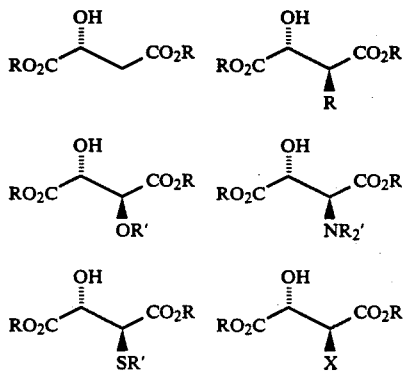

These compounds, and others which can be produced by reacting a tartrate cyclic sulfate diester or diamide of the present invention and an appropriate nucleophile, can be used to produce chiral synthons, such as α-amino-β-hydroxy acids, which can be further modified to produce antibiotics, and precursors of pheromones.

Different chiral diester compounds can be produced which have the same molecular formulae as those depicted above but which display the mirror image enantiomeric asymmetry. Rather than possessing the general enantiomeric form shown by general formula (2), they have the general enantiomeric form shown by general formula (3):

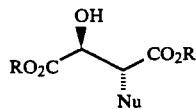
(3)

These compounds (enantiomers) can be produced when the D-(−)-tartaric acid diester is used as the starting material rather than the L-(+)-tartaric acid diester. That is, enantiomers with general formula (2) are produced when a diester of L-tartaric acid is the starting material and enantiomers when general formula (3) are produced when the same diester of D-tartaric acid is the starting material. The chemical reactions that produce these enantiomers are the same regardless of the enantiomeric identity of the tartaric acid starting material. In summary, the starting material is treated with a thionyl halide and then an oxidizing agent and a catalytic quantity of a ruthenium-containing compound are added in an appropriate solvent or solvent mixture. The resulting cyclic sulfate compound is then reacted with a selected nucleophile which opens the cyclic structure. Subsequent hydrolysis of the O-S bond yields the chiral diester compound of either general formula (2) or general formula (3) depending on which enantiomer of the tartaric acid diester was initially employed.

Where acid-sensitive functionalities are present on the diol, nucleophilic opening of the cyclic sulfates, which are unhindered or activated by an adjacent carbonyl group occurs at room temperature in usually less than 30 minutes. Selective hydrolysis of the sulfate esters in the presence of acid-labile groups, is effected by mild hydrolysis of the sulfates using a catalytic amount of acid in moist ethereal solvents. Hydrolysis of cyclic sulfates having acid-labile groups can be achieved, for example, in THF using a catalytic amount of concentrated sulfuric acid ($H_2SO_4$) in the presence of about 0.5 to 1.0 equivalents of water. Hydrolysis under these conditions was chemo-selective: all of the alcohol protecting groups remained intact after the hydrolysis of the sulfate esters were complete. A minimum amount of water is necessary to achieve the desired chemoselectivity.

Basically the synthesis of chiral synthons from tartaric acid, for example, involves either transformation of the ester groups, transformation of the hydroxyl groups, or transformation of both functions. These transformations include substitution, reduction, ring formation and chain shortening or elongation. Through these transformations, both hydroxyl and ester groups can be modified to produce many useful homochiral (optically pure) synthons such as those shown below:

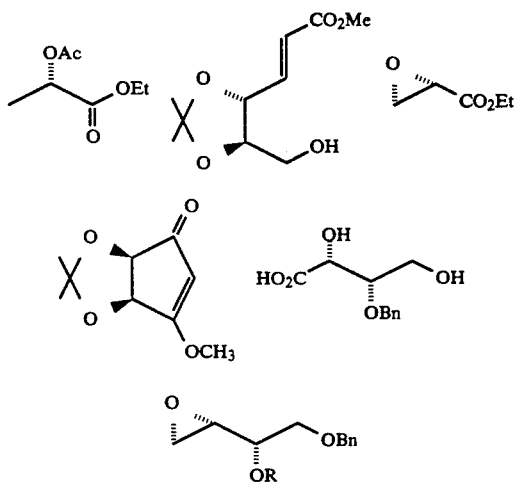

For example, this process can be used to synthesize β-hydroxyaspartate diesters, which are important chiral building blocks for β-lactam antibiotics. A nucleophile, such as a sodium azide, is reacted with a tartrate cyclic sulfate compound such as, for example, (−)-diethyl tartrate 2-3 cyclic sulfate. The reaction is carried out in an organic solvent or solvent mixture (e.g., acetone and water), which is capable of solvating all of the reagents. The nucleophilic attack in this reaction causes the opening of the sulfate ring resulting in the mono-substituted product after acidic hydrolysis (here, diethyl (2S,3R)-2-azido-3-hydroxysuccinate). This product is then reduced in the presence of a catalyst (e.g., palladium) to yield the diethyl L-erythro-β-hydroxyaspartate, which can be used without further purification.

Diethyl L-erythro-β-hydroxyaspartate can then be used to produce a number of biologically active nuclear analogs of β-lactam antibiotics using known synthetic procedures, such as the process described by Mattingly and Miller in *J. Organic Chemistry*, 48:3556–3559 (1983). Briefly, the substituted hydroxyaspartate diester is reacted with tert-butylpyrocarbonate to give the Boc-derivative (diethyl(tert-butoxycarbonyl)-β-hydroxyaspartate) which, upon coupling with o-benzylhydroxylamine, yields the desired hydroxyamate product. The hydroxyamate then undergoes diethylazodicarboxylate/triphenylphosphine-mediated cyclization to form β-lactam. β-lactams are an important class of antibiotics. This process can be used to form various optical isomers of β-lactams to synthesize a number of chiral β-lactam compounds of biological interest.

The compounds of the present invention can also be used as building blocks to form other substituted stereoisomers of β-hydroxyaspartate compounds.

Homochiral 1-2 cyclic sulfates produced by the present process can be used to synthesize homochiral aziridines and aminoalcohols. Primary amines react with the cyclic sulfates to give β-aminosulfates which can be converted either to aziridines or to aminoalcohols by treatment of with base or aqueous acid, respectively. For example, the reaction of cyclic sulfates with azide followed by reduction/cyclization with lithium aluminum hydride (LiAlH$_4$) yields optically active N-unsubstituted aziridines. Homochiral aziridines produced by this method are then used to form bioactive molecules.

Hydrolysis of the β-aminosulfates with 20% aqueous sulfuric acid (H$_2$SO$_4$) followed by adjustment of the pH to 10 with 20% sodium hydroxide (NaOH) gave aminoalcohols in good yield. The aziridines are stable to the above described hydrolytic conditions. The β-aminosulfates are not cyclized to the aziridines by treatment with 20% NaOH at room temperature, however, they do cyclize upon refluxing with 20% NaOH followed by steam distillation (Wenker Procedure). J. A. Deyrup, *In: Heterocycles*, Vol. 42, part 2, p. 1, A. Hussner, Ed.; John Wiley & Sons, NY, (1983). The formation of aziridines by deprotonation of the β-aminosulfates, either with n-BuLi or LiAlH$_4$, proceeds via S$_N$2 displacement of sulfate by the adjacent amino group. Formation of aziridines from cyclic sulfates is therefore assumed to occur with inversion at the stereogenic center(s). This assumption was proved in one case by independent synthesis of the aziridine from phenylalanine of known configuration (Table 1, entry 8). Homochiral N-unsubstituted aziridines are produced by simple alteration of the nucleophile. Thus, treatment of the cyclic sulfates with lithium azide (LiN$_3$) in THF gave the desired azidosulfates which, upon reduction with LiAlH$_4$ in refluxing THF followed by 20% KOH, afforded the N-unsubstituted homochiral aziridines in good yield, as shown in Table 3:

TABLE 3

| | Cyclic Sulfate Route to N-Unsubstituted Aziridines | | | | |
|---|---|---|---|---|---|
| | Cyclic Sulfates | | Overall yield | Aziridines $[\alpha]^{22}$D | |
| Entry | R' | R" | 2—>4 | (c in CHCl$_3$) | % ee[a] (abs. config.)[b] |
| 1 | (R)-Cyclohexyl | H | 80 | −11.76° (0.91) | >96 (S) |
| 2 | (R)-n-Butyl | (R)-n-Butyl | 88 | −23.43° (0.96) | 67[c] (SS) |

[a]The % ee is based in $^1$H and $^{13}$C NMR of Mosher amide derivatives.
[b]The absolute configuration has been assigned on the basis of assumed stereospecific inversion at the stereogenic center(s).
[c]The cyclic sulfate was derived from diol of 67% enantiomeric excess.

The present method provides an efficient route to form homochiral aziridines.

In this method, cyclic sulfates are treated with an excess of a primary amine in dry tetrahydrofuran (THF) to form β-aminosulfates, which are deprotonated and cyclized to form the aziridine by treatment with LiAlH$_4$ or n-BuLi. Several substituted homochiral aziridine compounds produced by this method are shown in Table 2:

In contrast to the formation of aminoalcohols or aziridines from cyclic sulfates, cyclopropane derivatives alternatively can be prepared from cyclic sulfate intermediates. For example, the reaction of 1,2-decane cyclic sulfate with the carbanion of dimethyl malonate formed with 2 equivalents of NaH gives a dimethylcarboxylate derivative of 1,2-decane cyclopropane. With refluxing dimethoxy ethane (DME) as the solvent for

TABLE 2

| | Cyclic Sulfate Route to N-Substituted Aziridines | | | | | |
|---|---|---|---|---|---|---|
| | Cyclic Sulfates | | | Aziridines Overall yield | $[\alpha]^{22}$D | | (abs. |
| Entry | R' | R" | RNH$_2$ | 2—>7[a] | (c in CHCl$_3$) | % ee/de[b] | config.)[b] |
| 1 | (R)-Cyclohexyl | H | PhCH$_2$NH$_2$ | 78 (77) | −1.85° (0.92) | >96 | (S) |
| 2 | (R)-Cyclohexyl | H | Ph(CH$_2$)$_3$NH$_2$ | 81 (79) | +3.21° (1.71) | >96 | (S) |
| 3 | (R)-Cyclohexyl | H | (S)-2-aminobutane | (79) | +25.16° (1.57) | >96 | (SS) |
| 4 | (R)-Cyclohexyl | H | (S)-2-methylbenzyl amine | 79 | −49.6° (1.2) | >96 | (SS) |
| 5 | (R)-n-Butyl | (R)-n-Butyl | PhCH$_2$NH$_2$ | 62 | −20° (0.86) | 67 | (SS)[c] |
| 6 | (R)-Phenyl | (R)-Phenyl | PhCH$_2$NH$_2$ | 73 (70) | −104.78° (1.41) | >96 | (SS) |
| 7 | (R)-Phenyl | (R)-Phenyl | (S)-2-aminobutane | (82) | −108.0° (2.0) | >96 | (SSS) |
| 8 | (R)-Benzyl | H | PhCH$_2$NH$_2$ | (81) | −2.60° (1.38) | 20 | (S)[d] |
| 9 | (R)-Benzyl | H | (S)-2-aminobutane | (89) | +13.84° (1.82) | 19 | (SS)[d,e] |

[a]The value in parentheses indicates the yield of aziridine obtained using LiAlH$_4$.
[b]The % de was determined by NMR spectroscopy. The % ee is assumed based on the optical purity of the starting diol used and has in one case been correlated by comparison with an authentic sample prepared from optically pure aminoacid [entry 8; $[\alpha]^{22}$D = −13.58° (c 1.59, CHCl$_3$)]$^8$. The other absolute configurations are assigned on the assumption of stereospecific inversion at the stereogenic center(s) of the cyclic sulfates.
[c]The cyclic sulfate was derived from diol of 67% enantiomeric excess.
[d]The cyclic sulfate was derived from diol of 20% enantiomeric excess.
[e]The $^{13}$C NMR indicates 19% de which is consistent with the 20% ee of the starting diol.

this reaction, the yield of this cyclopropane derivative can be improved (e.g., from 50% to 70%).

The regiochemical preferences of the nucleophilic opening of cyclic sulfates have been determined. The preference for opening at the position α to the carbonyl group is very high, in contrast to poor α selection observed in glycidic esters. This specificity can be applied, for example, to provide a variety of natural and unnatural α-amino β-hydroxy-acids by the opening of chiral cyclic sulfates by an azide ($N_3$) anion, followed by reduction.

The invention is further illustrated by the following examples, which are not to be seen as limiting in any way.

EXAMPLE 1

General Procedure for Synthesis of Cyclic Sulfate

A three neck round-bottomed flask equipped with a reflux condenser and topped with a $CaCl_2$ drying tube, a stopper and a rubber septum was charged with about 1.0 equiv. of the 1,2-diol and 1–4 ml of carbon tetrachloride ($CCl_4$) per mmol substrate. Thionyl chloride ($SOCl_2$) (Aldrich) in an amount of 1.2–1.5 equiv. was added via a syringe, and the resulting solution or suspension was heated at about 60° C. to reflux until no 1,2-diol was left (the reaction was monitored by TLC). The solution was cooled with an ice bath and diluted with an equal amount of acetonitrile ($CH_3CN$) and 1.5 times the amount of water. Ruthenium chloride ($RuCl_3.H_2$) (Aldrich) in an amount of between 0.001–0.01 equiv. and 1.5–2.0 equiv. of sodium periodate ($NaIO_4$) were added, and the mixture was stirred at room temperature until the reaction was complete. The mixture was then diluted with ether or methylene chloride ($CH_2Cl_2$) and the phases were separated. The organic phase was washed with $H_2O$, saturated aqueous sodium bicarbonate ($NaHCO_3$), brine, and dried over magnesium sulfate ($MgSO_4$). The solution was filtered through a pad of Celite and silica gel to remove the brown color and concentrated under a vacuum. The product thus obtained was usually pure and could be used without further purification or could be purified by chromatography on silica gel or by recrystallation.

EXAMPLE 2

Preparation of 1,2-Decanediol Cyclic Sulfate

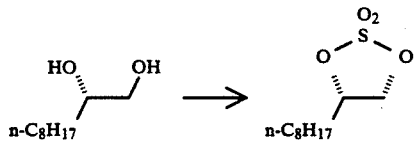

Preparation of 1,2-decanediol cyclic sulfate was carried out as described in Example 1. Thionyl chloride (5.5 mL, 75 mmol) was added to a suspension of 1,2-decanediol (8.71 g, 50 mmol) in $CCl_4$ (50 ml), and the resulting solution was heated to reflux for 20 min. The solution was then cooled with ice-water and $CH_3CN$ (50 ml) and water (75 ml) were added. After addition of $RuCl_3.3H_2O$ (130 mg, 0.5 mmol) and $NaIO_4$ (21.4 g, 100 mmol), the mixture was stirred for 10 min. at room temperature. The mixture was then extracted with ether (250 ml), and the combined organic solution was washed with water, saturated $NaHCO_3$ and brine. After drying over $MgSO_4$, the solution was filtered through a pad of Celite and silica gel and concentration to give a pale yellow oil. The oil was purified by kugelrohr distillation to give 1,2 decanediol cyclic sulfate as a colorless oil in a yield of over 90% (10.81 g, 91.5%). The product had the following properties: IR (film): 2940, 2860, 1470, 1390, 1210, 1000, 840 cm$^{-1}$; $^1$H NMR ($CDCl_3$) δ 4.92–5.05 (m, 1H), 4.70 (dd, J=5.9, 8.6 Hz, 1H), 4.34 (t, J=8.4 Hz, 1H), 1.90–2.04 (m, 1 H), 1.68–1.85 (m, 1H), 1.20–1.45 (m, 12H), 0.89 (t,J=6.44 Hz, 3H). Analysis calculated for the formula $C_{10}H_{20}O_4S$: C, 50,83%; H, 8.53%. Actual results: C, 51.16%, H, 8.30%.

Using a similar procedure, 1,2-decanediol cyclic sulfite (2.10 g, 10 mmol) was oxidized with sodium hypochlorite (NaOCl) (Clorox , 5% active chlorine; 37 g) catalyzed by $RuCl_3.3H_2O$ (58 mg, 0.22 mmol) in $CCl_4$ (23 ml) and $CH_3CN$ (23 ml) at 0° C. to room temperature. After 40 min., the reaction was worked up as above to give 1,2 decanediol cyclic sulfate as a pale yellow oil in a yield of over 90% (2.24 g, 95%).

EXAMPLE 3

Preparation of (2S*,3S*)-3-(2-Methyl phenoxy)-3-phenyl-1,2-propanediol cyclic sulfate

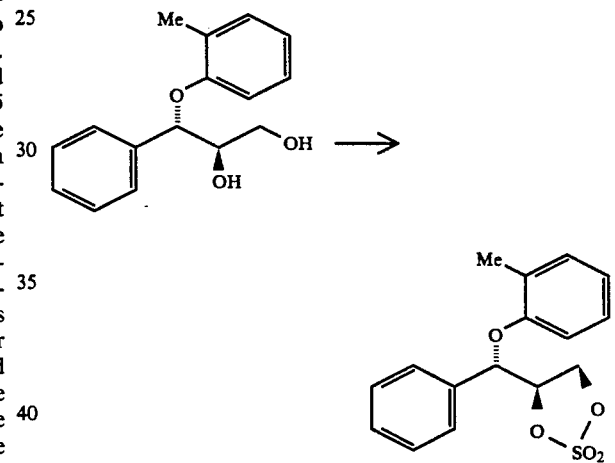

Thionyl chloride (0.50 mL, 6.8 mmol) was added to a solution of 3-(2-methylphenoxy)-3-phenyl-1,2-propanediol (1.46 g, 5.66 mmol) in $CH_2Cl_2$ (25 ml), and the solution was refluxed for 30 min. After removal of solvent, the corresponding 1,2-cyclic sulfite was obtained (1.54 g, 90%). The cyclic sulfite (608 mg, 2.0 mmol) was then dissolved into a $CH_3CN$-$CCl_4$-$H_2$ solution (4–4–6 ml) and $RuCl_3.3H_2O$ (12 mg, 0.044 mmol) and $NaIO_4$ (856 mg, 4.0 mmol) were added. The mixture was stirred at room temperature for 15 min. and then extracted with ether (2×60 ml). The combined ethereal solution was washed with water (10 ml), saturated aqueous $NaHCO_3$ (10 ml), and brine (10 ml). After dried over $MgSO_4$, the solution was filtered through a pad of Celite and silica gel. After removal of solvent, the crude product was purified by chromatography (20% EtOAc/hexane) to give (2S*, 3S*)-3-(2-methylphenoxy)-3-phenyl-1,2 propane diol cyclic sulfate as a white solid in a yield of 90% (578 mg, 90%). The product had the following properties: IR($CHCl_3$): 3000, 1605, 1590, 1495, 1390, 1240, 1215, 1200, 1125, 990, 920, 810, 755, 710 cm$^{-1}$; $^1$H NMR ($CDCl_3$) δ 7.37–7.43 (m, 5H), 7.16 (d,J=7.35 Hz, 1H), 6.97 (dt,J=1.55 Hz, 6.92 Hz, 1H), 6.87 (de,J=0.91 Hz, 6.46 Hz, 1H), 6.53 (d,J=7.95 Hz, 1H), 5.51 (d,J=5.43 Hz, 1H), 5.11

(ddd, J=5.43, 6.2, 6.7 Hz, 1H), 4.98 (dd, J=6.7, 8.7 Hz, 1H), 4.70 (dd, J=6.2, 8,7 Hz, 1H), 2.34 (s, 3H). Analysis calculated for the formula $C_{16}H_{16}O_5S$: C, 59.98%, H, 5.04%. Actual results: C, 58.73%; H, 5.05%.

EXAMPLE 4

Preparation of (2S*,3S*)-3-Isopropyl oxy-1,2-undecanediol cyclic sulfate

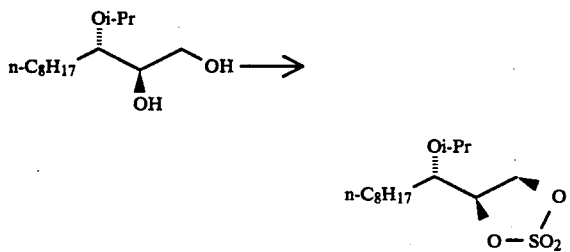

Thionyl chloride (0.22 ml, 4.6 mmol) was added to a solution of 3-isopropyloxy-1,2-undecanediol (0.94 g, 3.80 mmol) in $CH_2Cl_2$ (20 ml). The solution was refluxed for 20 min. and then concentrated under reduced pressure. $CH_3CN$ (3 ml), $CCl_4$ (4 ml) and water (6 ml) were added, followed by $RuCl_3.3H_2O$ (10 mg, 0.038 mmol) and $NaIO_4$ (1.63 g, 7.6 mmol). The mixture was stirred for 15 minutes at room temperature and then extracted with ether (2×50 ml). The combined ethereal solution was washed with water (10 ml), saturated $NaHCO_3$ (10 ml), and brine (10 ml). After dried over $MgSO_4$, the solution was filtered through a pad of Celite and silica gel. After removal of solvent, the crude product was purified by silica gel chromatography (20% EtOAc/hexane) to give (2S*,3S*)-3-isoproploxy-1,2-undecanediol cyclic sulfate as a colorless oil in a yield of over 90% (1.11 g, 95%). The product had the following properties: IR (film): 2920, 2860, 1470, 1395, 1220, 1120, 990, 860 cm$^{-1}$; $^1H$ NMR ($CDCl_3$) 4.62-4.83 (m, 3H), 3.75-3.79 (m, 2H), 1.40-1.48 (m, 2 HO, 1.28 (br.s, 10H), 1.20 (t,J=6.92 Hz, 6H), 0.88 (t, J=6.87 Hz, 3H). Analysis calculated for the formula $C_{14}H_{28}O_5S$: C, 54.52%; H, 9.15%. Actual results: C, 54.65%; H, 8.85%.

EXAMPLE 5

Preparation of (+)-(2S,3S)-3-(2-Ethoxy phen-oxy)-3-phenyl-1,2-propanediol cyclic sulfate

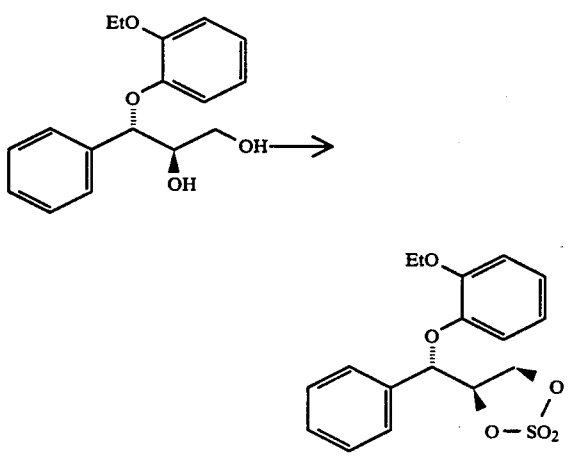

Thionyl chloride (0.66 ml, 9.0 mmol) was added to a solution of 3-(2-ethoxylphenoxy)-3-phenyl-1,2-propanediol (1.15 g, 4.0 mmol) in $CH_2Cl_2$ (25 ml), and the solution was refluxed for 2 hours. After evaporation of excess $SOCl_2$ and solvent, the crude product was dissolved into $CH_3CN$—$CCl_4$—$H_2O$ solution (8-8-12 ml). $RuCl_3.3H_2O$ (23 mg, 0.09 mmol) and $NaIO_4$ (1.71 g, 8.0 mmol) were added. After stirred at room temperature for 15 min., the mixture was extracted with $CH_2Cl_2$ (4×40 ml), and the combined organic phases were washed with water, saturated $NaHCO_3$ and brine. After drying over $MgSO_4$, the solution was concentrated to give a solid which was recrystallized from t-butyl methyl ether to yield (+)-(2S,3S)-3-(2-ethoxy-phenoxy)-3-phenyl-1,2-propanediol cyclic sulfate as a white solid in a yield of over 80% (1.19 g, 85%). The product had the following properties: mp 96°-98° C.; $[\alpha]^{23}D+100.75°$ (c 1.73, $CHCl_3$); IR (Nujol): 3040, 1500, 1265, 1210, 1200, 1120, 1045, 1015, 950, 930, 910, 805, 780, 765, 755, 745, 710 cm$^{-1}$; $^1H$ NMR ($CDCl_3$) 67 7.36-7.46 (m, 5H), 6.92-7.00 (m, 1H), 6.86 (d,J=8.0 Hz, 1 H), 6.69 (d,J=3.88 Hz, 2H); 5.29-5.35 (m, 2H), 5.05-5.13 (m, 1H), 4.86 (dd, J=6.4, 8.9 Hz, 1H), 4.07 (q,J=6.28 Hz, 2H), 1.46 (t,J=6.28 Hz, 3 H). Analysis calculated for the formula $C_{17}H_{18}O_6S$: 58.27%; H, 5.18%; S, 9.15%. Actual results: C, 58.27%; H, 5.10%; S, 9.05%.

EXAMPLE 6

Preparation of 3-Undecanyl Nitrato-1,2-Cyclic Sulfate

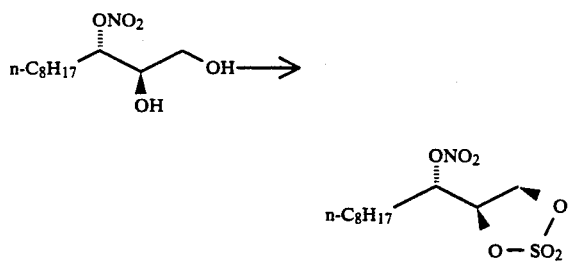

Thionyl chloride (1.0 ml, 13.7 mmol) was added to a solution of 1,2-dihydroxy-3-undecanyl nitrate (1.70 g, 6.8 mmol) in $CH_2Cl_2$ (25 ml), and the solution was refluxed for 20 min. After evaporation of excess $SOCl_2$ and solvent, the crude product was dissolved into $CH_3CN$—$CCl_4$—$H_2O$ solution (10-10-15 ml). $RuCl_3.3H_2$ (40 mg, 0.15 mmol) and $NaIO_4$ (2.91 g, 13.6 mmol) were added. After stirring at room temperature for 10 min., the mixture was extracted with $CH_2Cl_2$ (4×50 ml), and the combined organic solution was washed with water, saturated aqueous $NaHCO_3$ and brine. After drying over $MgSO_4$, the solution was concentrated, and the crude product was purified by chromatography (20% EtOAc in hexane) to give 3-undecanyl nitrate-1,2-cyclic sulfate as a pale yellow oil in a yield of over 70% (1.56 g, 74%). The product had the following properties: IR (film): 2930, 2860, 1650, 1465, 1400, 1280, 1215, 1000, 830 cm$^{-1}$; $^1H$ NMR ($CDCl_3$) δ 5.40 (m, 1H), 4.95-5.05 (m, 1H), 4.76 (dd, J=7.1, 5.2 Hz, 1H), 4.61 (dd,J=6.0, 7.1 Hz, 1H), 1.64-1.76 (m, 2H), 1.19-1.54 (m, 12H), 0.89 (t,J=7.8 Hz, 3H).

EXAMPLE 7

Preparation of 5,6-Decanediol Cyclic Sulfate

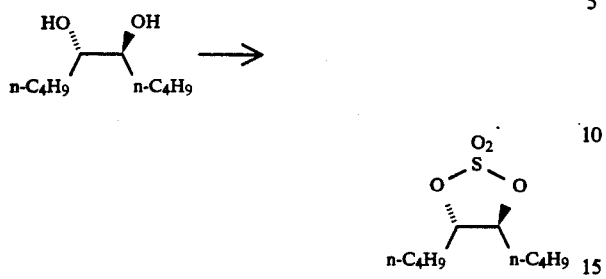

The reaction was performed as described in the general procedure in Example 1, in this case with 0.87 g (5.0 mmol) of syn-5,6-decanediol in 10 ml of CCl$_4$, 10 ml of CH$_3$CN and 15 ml of water using 0.44 ml (6.0 mmol) of SOCl$_2$ (20 min. at 60° C.), 1.60 g (7.5 mmol) of NaIO$_4$ and 3.0 mg (0.01 mmol) of RuCl$_3$.3H$_2$O (2 hours at room temperature). The crude product was purified by chromatography (5% EtOAc in hexane) to yield 5,6-decanediol cyclic sulfate as a colorless oil (1.05 g, 88.7%). The product had the following properties: IR (film): 2955, 2867, 1476, 1383 1206 956 900 828 cm$^{-1}$; $^1$H NMR (CDCl$_3$) δ 4.55 (m, 2H), 1.30–1.90 (m, 12H), 0.90 (t,J=6.77 Hz, 6H). Analysis is calculated for the formula C$_{10}$H$_{20}$O$_4$S: C, 50.82%; H, 8.53%; S, 13.57%. Actual results: C, 51.05%; H, 8.58%; S, 13.24%.

EXAMPLE 8

Preparation of Cyclohexyl Glycidate-2,3-Cyclic Sulfate

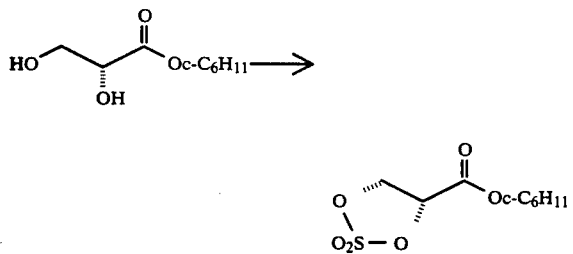

The reaction was performed as described in the general procedure in Example 1, in this case with 1.50 g (8.0 mmol) of cyclohexyl 2,3-dihydroxyglycidate in 10 ml of CCL$_4$, 15 ml of CH$_3$CN and 15 ml of water using 0.70 ml (9.6 mmol) of SOCl$_2$ (50 min. at 60° C.), 2.57 g (12.0 mmol) of NaIO$_4$ and 3.0 g (0.01 mmol) of RuCl$_3$.3H$_2$O (50 min. at room temperature). After separation and washing, the product was purified by filtration through silica gel (ether) to yield cyclohexyl glycidate-2,3-cyclic sulfate (1.76 g, 88%). The product had the following properties: mp 55°–57° C.; IR (film): 2933, 2856, 1739, 1450, 1394, 1205, 1072, 1033, 833 cm$^{-1}$; $^1$H NMR (CDCl$_3$) δ 5.20 (dd,J=7.3, 12.8 Hz, 1H), 4.78–5.00 (m, 3H), 1.20–1.90 (m, 10H). Analysis calculated for the formula C$_9$H$_{14}$O$_6$S: C, 43.19%; H, 5.64%; 2, 12.81%. Actual results: C, 43.48%; H, 5.40%; S, 12.53%.

EXAMPLE 9

Preparation of Methyl Octadecanoate-2,3-Cyclic Sulfate

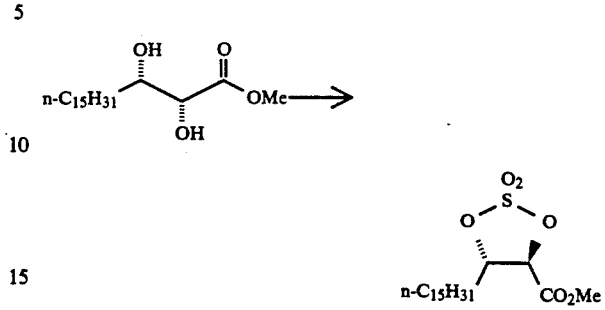

Thionyl chloride (0.09 ml, 1.2 mmol) was added to a solution of methyl 2,3-dihydroxy octadecanoate (0.33 g, 1.0 mmol) in CCl$_4$ (2 ml) and the resulting solution was heated at about 60° C. for 10 min. The solution was then cooled with an ice-water bath and CH$_3$CN (2 ml) and water (3 ml) were added. After addition of RuCl$_3$.3H$_2$O (1.0 mg, 0.01 mmol) and NaIO$_4$ (0.32 g, 1.5 mmol), the mixture was stirred for 20 min. at room temperature. The mixture was then extracted with ether (100 ml) and the ethereal solution was washed with water, saturated aqueous NaHCO$_3$ and brine. After drying with MgSO$_4$, the solution was filtered through a pad of Celite and silica gel and concentated to give methyl octadecanoate-2,3-cyclic sulfate as a white solid (0.373 g, 95%). The product had the following properties: mp 44.5°–46° C.; IR (Nujol): 2920, 1778, 1765, 1205, 1050 cm$^{-1}$; $^1$H NMR (CDCl$_3$): δ 4.87–4.97 (m, 1H), 4.85 (d,J=7.30 Hz, 1H), 3.88 (s, 3H), 1.91–2.00 (m, 2H), 1.37–1.54 (m, 2H), 1.24 (m, 24H), 0.86 (t,J=5.78 Hz, 3H). Analysis calculated for the formula C$_{19}$H$_{36}$O$_6$S: c, 58.13%; H, 9.24%; S, 8.17%. Actual results: C, 58.19%; H, 9.02%; S, 7.92%.

EXAMPLE 10

Preparation of Ethyl 3-Cyclohexyl Propionate-2,3-Cyclic Sulfate

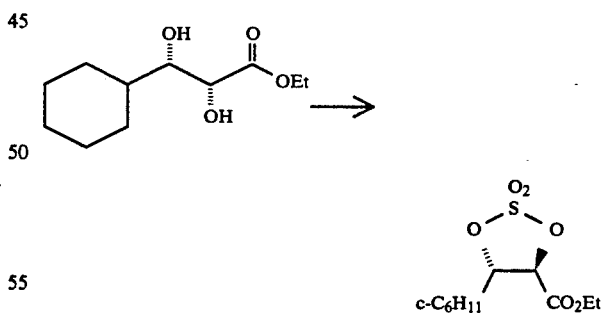

The reaction was performed as described in the general procedure in Example 1, in this case with 1.08 g (5.0 mmol) of ethyl 3-cyclohexyl-2,3-dihydroxypropionate in 10 ml of CCl$_4$, 10 ml of CH$_3$CN and 15 ml of water using 0.44 ml (6.0 mmol) of SOCl$_2$ (30 min. at 60° C.), 1.60 g (7.5 mmol) of NaIO$_4$ and 6.0 mg (0.025 mmol) of RuCl$_3$.3H$_2$O (1 hour at room temperature). After separation, washing and filtering as described in the general procedure, ethyl 3-cyclohexyl propionate-2,3-cyclic sulfate was obtained as a colorless oil (1.35 g, 97%). The product had the following properties: IR (film): 2920, 2850, 1750, 1450, 1400, 1300, 1210, 1050, 975, 940 cm$^{-1}$; $^1$H NMR (CDCl$_3$): δ 4.94 (d,J=6.30 Hz, 1H), 4.76 (dd,J=6.30; 6.55 Hz, 1H), 4.32 (q,J=7.2 Hz, 2H), 1.68 (m, 6H), 1.34 (t,J=7.2 Hz, 3H), 1.14–1.25 (m, 5H). Analysis calculated for the formula C$_{11}$H$_{18}$O$_6$S: C, 47.47%; H, 6.52%; S, 11.52%. Actual results: C, 47.95%; H, 6.37%; S, 11.51%.

EXAMPLE 11

Preparation of N-Benzyl Glycidamide-2,3-Cyclic Sulfate

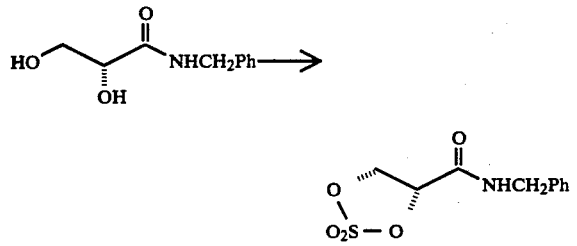

The reaction was performed as described in the general procedure in Example 1, in this case with 0.88 g (4.5 mmol) of N-benzyl 2,3-dihydroxyglycidamide in 10 ml of CCl$_4$, 15 ml of CH$_3$CN and 15 ml of water using 0.40 ml (5.4 mmol) of SOCl$_2$ (50 min. at 60° C.), 1.44 g (6.8 mmol) of NaIO$_4$ and 3.0 mg (0.01 mmol) of RuCl$_3$.3H$_2$O (30 min. at room temperature). After separation and washing the product was purified by filtration through silica gel (ether) to yield N-benzyl glycidamide-2,3-cyclic sulfate as a yellow solid (0.74 g, 63.8%). The product had the following properties: mp 95°–97° C.; IR (Nujol): 3288, 1667, 1556, 1454, 1378, 1209, 1020, 947 846, 738, 694 cm$^{-1}$; $^1$H NMR (CDCl$_3$) δ 7.20–6.45 (m, 5H), 6.75 (bs, 1H), 5.20–5.30 (m, 1H), 4.80–5.00 (m, 2H), 4.40–4.60 (m, 2H).

EXAMPLE 12

Preparation of (−)-Diisopropyl Tartrate 2,3-Cyclic Sulfate (−)-Diisopropyl tartrate 2,3-cyclic sulfate was prepared as described below. The reaction of tartrate diesters in general can be represented as follows:

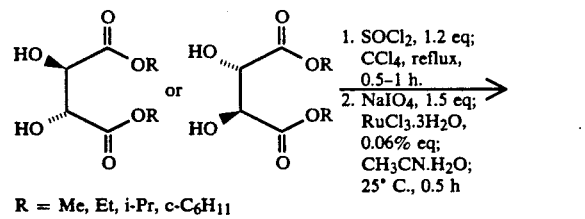

R = Me, Et, i-Pr, c-C$_6$H$_{11}$

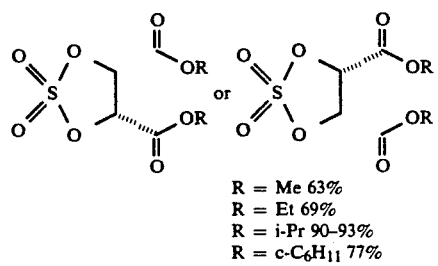

R = Me 63%
R = Et 69%
R = i-Pr 90–93%
R = c-C$_6$H$_{11}$ 77%

Method A: A 250 ml three neck round-bottomed flask equipped with a reflux condenser, a CaCl$_2$ drying tube, a stopper and rubber septum, was charged with 11.72 grams (50.0 mmol) (+)-diisopropyl tartrate [(+)-DIPT] (Aldrich), and 50 ml of carbon tetrachloride (CCl$_4$). Thionyl chloride (SOCl$_2$), 4.4 ml (60.0 mmol) (Fluka) was then added with a syringe, and the solution refluxed for 30 minutes, or until no DIPT is left. The disappearance of DIPT was followed by thin layer chromatography TLC). The solution was cooled with an icewater bath and diluted with 50 ml of acetonitrile (CH$_3$CN), and 75 ml of water (H$_2$O). Ruthenium chloride (RuCl$_3$.3H$_2$O) 8 mg, (0.03 mmol) (Aldrich) and sodium periodate (NaIO$_4$) 16.0 g, (75.0 mmol) (Aldrich) were then added. The resulting orange solution was stirred at room temperature for 40 minutes, until the reaction was complete as indicated by formation of a yellow solution. The reaction was monitored by thin layer chromatography (20% EtOAc in hexane).

The mixture was diluted with 400 ml of ether and the aqueous layer was separated. The organic layer was then washed once with 50 ml H$_2$O, twice with 50 ml of saturated sodium bicarbonate (NaHCO$_3$) and once with 30 ml of brine, and dried over magnesium sulfate (MgSO$_4$). The solution was then filtered through a pad of Celite and silica gel and concentrated to give (−)-diisopropyl tartrate 2,3-cyclic sulfate as a colorless liquid in a yield of over 90% (13.8g, 93.2%). The product had the following properties: optical rotation, [α]$^{23}$D −71.43° (c 4.41, CHCl$_3$);IR(neat): 2980, 2940, 2880, 1740, 1460, 1450, 1410, 1280, 1250, 1210, 1145, 1100, 1060, 1010, 950, 850, 830, 770 cm$^{-1}$; $^1$H NMR(CDCl$_3$) δ 5.38(s, 2H),5.20(m, 2H),1.32 (d,d,J=6.21 Hz, 12H); Analysis calculated for the formula C$_{10}$H$_{16}$O$_8$S: C,40.53%; H,5.44%; S,10.82%. Actual results: C,40.79%; H,5.32%; S,10.68%.

Method B represents a variation of Method A. Method B: Thionyl chloride (4.4 ml, 60 mmol) was added to a solution of (+)-DIPT in CCl$_4$ (50 ml) and the resulting solution was heated to reflux for 30 minutes. The solution was then cooled with an ice-water bath and diluted with CH$_3$CN (50 ml). RuCl$_3$.3H$_2$O (8 mg, 0.03 mmol) and NaIO$_4$ (16 g, 75 orange mixture was stirred at room temperature for 60 minutes, and the resulting yellow solution was diluted with ether (400 ml). Separation and washing was performed as described in Method A, and the product was filtered through Celite and silica gel to yield (−)-diisopropyl tartrate 2,3-cyclic sulfate as a colorless oil (13.6 g, 92%).

EXAMPLE 13

Preparation of (−)-Dimethyl Tartrate 2,3 Cyclic Sulfate

Preparation of (−)-dimethyl tartrate 2,3-cyclic sulfate was carried out as described in Method B in Example 12, except that 50 mmol of (+) -dimethyl tartrate was used. The product was obtained as a white solid with a yield of 63.3% and had the following properties: optical rotation, [α]$^{23}$D −70.50° (c2.01;CHCl$_3$); IR(neat):
1755,1400,1350,1308,1260,1225,1218,1080,1050,1020 975,958,890,850,815cm$^{-1}$; $^1$HNMR(CDCl$_3$) 5/49 (S.2H), 392(S.6H); Analysis calculated for the formula C$_6$H$_8$O$_8$S: C, 30.00%; H, 3.36%; S, 13.35% . Actual results: C,30.26%; H,3.13%; S,13.26%.

EXAMPLE 14

Preparation of (−)-Diethyl Tartrate 2,3 Cyclic Sulfate

Preparation of (−)-diethyl tartrate 2,3-cyclic sulfate was carried out as described in Method B in Example 12 except that 50 mmol of (+)-diethyl tartrate was used. The product was obtained as a white solid with a yield of 69.4% and had the following properties: optical rotation $[\alpha]^{23}D$ −74.6° (c2.43,CHCl$_3$). IR (Nujol): 1755, 1390, 1250, 1210, 1050, 940, 850, 780 cm$^{-1}$; $^1$H NMR (CDCl$_3$) δ 5.44 (s, 2H), 4.36 (q,J=7.32 Hz, 4H), 1.35 (t,=7.32 Hz, 6H). Analysis calculated for the formula $C_8H_{12}O_8 9S$: c, 35.82%; H, 4.51%; S, 11.95%. Actual results: C, 35.79%; H, 4.28%; S, 11.81%. Compound could be recrystallized from ether and tert-butyl methyl ether to give hexagonal crystals.

EXAMPLE 15

Preparation of (+)-Diisopropyl Tartrate 2,3-Cyclic Sulfate

Preparation of (+)-diisopropyl tartrate 2,3-cyclic sulfate was carried out as described in Method A in Example 12, except that 50.0 mmol of (−)-diisopropyl tartrate was used. The product was obtained with a yield of 92% and had the following properties: optical rotation, $[\alpha]^{23}D$ +71.66° (c5.36,CHCl$_3$). This product is the enantiomer of the product described in Example 12, so all of the spectroscopy and analytical data is the same.

EXAMPLE 16

Preparation of (−)-Dicyclohexyl Tartrate 2,3-Cyclic Sulfate

Preparation of (−)-dicyclohexyl tartrate 2,3-cyclic sulfate was carried out as described in Method B in Example 12 except that 50 mmol of (+) -dicyclohexyl tartrate was used. The product was obtained as a white solid with a yield of 76.6% and had the following properties: optical rotation, $[\alpha]^{23}D$ −64.8° (c2.25,CHCl$_3$). IR (Nujol): 2920, 2852, 1768, 1741, 1454, 1396, 1285, 1258, 1210, 1059, 1000, 938, 852, 774 cm$^{-1}$; $^1$H NMR (CDCl$_3$) δ 5.40 (s, 2 H), 4.90–5.05 (m, 2 H), 1.2–1.96 (m, 20 H). Analysis calculated for the formula $C_{16}H_{25}O_8S$: C, 51.05%; H, 6.43%; S, 8.52%. Actual results: C, 51.20%; H, 6.33%; S, 8.61%.

The experimental procedures described in Examples 12-16 were used to synthesize the dimethyl, diethyl-, and di-isopropyl and di-cyclohexyl disubstituted tartrate esters. Some of the properties of these four compounds are shown in Table 4:

TABLE 4

Preparation of Tartrate Cyclic Sulfates

| Tartrate | Cyclic Sulfate [a] | Method [b] | Yield % [c] | $[\alpha]^{23}D$ CH$_3$Cl | MP °C. |
|---|---|---|---|---|---|
| (+)-dimethyl tartrate | (−)-dimethyl tartrate 2,3 cyclic sulfate | A | 63.3 | −70.5°, c. 2.01 | 70–71 |
| (+)-diethyl tartrate | (−)-diethyl tartrate 2,3 cyclic sulfate | A | 69.4 | −74.6°, c. 2.43 | 74.5–75.5 |
| (+)-diisopropyl tartrate | (−)-diisopropyl tartrate 2,3 cyclic sulfate | B | 93.0 | −71.4°, c. 4.41 | liq. |
| (+)-dicyclohexyl | (−)-dicyclohexyl tartrate | A | 76.6 | +64.84°, c. 2.25 | 54–55 |

[a] All products were fully characterized and gave satisfactory spectral data
[b] A: water was added last
B: NaIO$_4$ was added last. See experimental procedure
[c] Yields are isolated yields.

EXAMPLE 17

Reactions of Tartrate Cyclic Sulfates with Nucleophiles

The tartrate cyclic sulfate compounds formed as described in Example 12, react with nucleophiles to yield a variety of substituted mono-sulfate salts. Further in situ acid hydrolysis of the mon-substituted products yields the beta-substituted erythro malate esters.

A variety of nucleophiles can be used in the present method. For example, benzyl, methyl or other alkyl groups can be added by reaction of the tartrate cyclic sulfate with Grignard reagents (e.g., benzyl magnesium chloride or methyl magnesium bromide); azide groups (N$_3$) can be added by reaction with sodium azide (NAN$_3$) and fluorine (F) can be added by reaction with tetraethyl ammonium fluoride (Et$_4$NF). Some of the nucleophilic reactions are summarized in Table 5 below.

TABLE 5

Reactions of Cyclic Sulfates with Nucleophiles

| Cyclic Sulfate | Nucleophile | Reaction Conditions [a] | Yield [%] [b] | $[\alpha]^{23}D$ CH$_3$Cl |
|---|---|---|---|---|
| (−)-dimethyl tartrate 2,3-cyclic sulfate | PhCH$_2$ | PhCH$_2$MgCl, 2.0 eq. Li$_2$CuCl$_4$, 10% eq. THF—DME, −78° C., 5 h. | 33.0 | −21.45 c1.10 |
| (−)-diethyl tartrate 2,3-cyclic sulfate | PhCH$_2$ | PhCH$_2$MgCl, 2.0 eq. Li$_2$CuCl$_4$, 10% eq. THF—DME, −78° C., 5 h. | 50.0 | −13.46 c1.79 |
| (−)-diisopropyl tartrate 2,3 cyclic sulfate | PhCH$_2$ | PhCH$_2$MgCl, 1.5 eq. Li$_2$CuCl$_4$, 1% eq. THF, −78° C., 2 h. | 73.0 | −8.95 c2.09 |
| (+)-diisopropyl tartrate 2,3-cyclic sulfate | N$_3$ | NaN$_3$, 2.0 eq. Acetone-H$_2$O 0–25° C., 1 hr. | 81.0 | +7.29 c3.73 |
| (−)-diisopropyl tartrate 2,3-cyclic sulfate | SCN | NH$_4$SCN, 2.0 eq. Acetone, 25° C., 12 h. | 87.0 | −8.77 c3.00 |
| (+)-diisopropyl | PhCO$_2$ | PhCO$_2$NH$_4$, 2.0 eq. | 94.6 | +17.43 |

TABLE 5-continued

Reactions of Cyclic Sulfates with Nucleophiles

| Cyclic Sulfate | Nucleophile | Reaction Conditions [a] | Yield [%] [b] | $[\alpha]^{23}D$ $CH_3Cl$ |
|---|---|---|---|---|
| tartrate 2,3-cyclic sulfate | | Acetone, 25° C., 12 h. | | c1.83 |
| (−)-diisopropyl tartrate 2,3-cyclic sulfate | $NO_3$ | $nBu_4N.NO_3$, 1.0 eq. $NH_4NO_3$, 1.0 eq. Acetone, 25° C., 12 h. | 93.0 | −22.98 c2.42 |
| (−)-diisopropyl tartrate 2,3-cyclic sulfate | F | $Et_4NF2H_2O$, 1.0 eq. $NH_4HF_2$, 1.0 eq. Acetone, 25° C., 12 h. | 89.0 | −12.32 c2.11 |
| (+)-diisopropyl tartrate 2,3-cyclic sulfate | H | $NaBH_3CN$, 2.0 eq. pH 4–5, THF, 65° C., 5 h. | 55.0 | +10.77 c2.47 |

[a] After reactions were complete, the sulfate salts were hydrolyzed in situ with 20% sulfuric acid.
[b] Yields are isolated and purified yields. All compounds were characterized by IR, $^1$HNMR spectroscopy and elemental analysis.

General Procedure:

The cyclic sulfate (1.0 equiv.) was dissolved in a solvent (about 0.1–0.5M) and the nucleophile (1.5–2.0 equiv.) was added at room temperature or 0° C. (for $N_3^-$). The resulting solution or suspension was then stirred at room temperature until no starting cyclic sulfate was left (the reaction was monitored by TLC). The solvent was then evaporated; ether (less than 5 ml per 1.0 mmol substrate) and $H_2SO_4$ (20% solution, less than 5 ml per 1.0 mmol substrate) were added to the flask. The resulting solution was stirred at room temperature for 6–12 hours (heating accelerating the hydrolysis). The solution was then extracted with ether or $CH_2Cl_2$ and the combined organic phases were washed with $H_2O$, and brine and dried over $MgSO_4$. After concentration, the crude product was purified by chromatography on silica gel to obtain the desired product.

EXAMPLE 18

Reaction of (−)-diisopropyl tartrate 2,3-cyclic sulfate with $NaN_3$

Following the general procedure described in Example 17, a solution of the cyclic sulfate (0.60 g, 2.0 mmol) and $NaN_3$ (200 mg, 3.0 mmol) in water (5 ml) and acetone (5 ml) was stirred at 0° C. to room temperature for 1 hour. After the solvent (acetone) was evaporated, the residue was hydrolyzed with $H_2SO_4$ (20%, 10 ml) in ether for 6 hours at room temperature. After extraction and washing, the crude product was purified on silica gel (20% EtOAc in hexane) to give diisopropyl (2S,3R)-2-azido-3-hydroxysuccinate as a colorless oil in a yield of over 80% (420 mg, 81%). The product had the following properties: optical rotation $[\alpha]^{23}D$ +7.29° (c3.73,$CHCl_3$); IR (film): 3470, 2980, 2940, 2880, 2120, 1735, 1470, 1450, 1390, 1375, 1220, 1100, 1010, 985, 935, 910, 900, 820 cm$^{-1}$; $^1$HNMR ($CDCl_3$) δ 5.09–5.14(m,2H),4.56(dd,J=2.4,4.0 Hz,1H),4.24 (d,J=2.35 Hz, 1H),3.27(t,J=5.00 Hz,1H), 1.28–1.31(m,12H). Analysis Calculated for the formula $C_{10}H_{17}N_3O_5$: C,46,32%; H,6.61%; N,16.21%. Actual results: C,46.50%; H,6.34%; N,15.95%.

EXAMPLE 19

Reaction of (−)-diisopropyl tartrate-2,3-cyclic sulfate with $NH_4SCN$

Following the general procedure described in Example 17, a solution of the cyclic sulfate (0.30 g, 1.0 mmol) and $NH_4SCN$ (152 mg, 2.0 mmol) in acetone (5 ml) was stirred at 0° C. to room temperature for 4.5 hours. After the solvent (acetone) was evaporated, the residue was hydrolyzed with $H_2SO_4$ (20%, 5 ml) in ether for 6 hours at room temperature. After extraction and washing, the crude product was purified on silica gel (20% EtOAc in hexane) to give diisopropyl (2R,3S)-2-hydroxy-3-thiocyanatosuccinate as an orange oil in a yield of over 85% (240 mg, 87%). The product had the following properties: optical rotation $[\alpha]^{23}D$ −8.77° (c3.00,$CHCl_3$); IR (film): 3460, 2980, 2930, 2880, 2150, 2060, 1720, 1460, 1450, 1370, 1250, 1180, 1140, 1100, 1010, 970, 920, 900, 860, 820, 735, 660 cm$^{-1}$; $^1$HNMR($CDCl_3$) 5.03–5.20(m, 2H) ,4.60(d,J=2.76 Hz , 1H) , 4.54 (d, J=2.50 Hz , 1H) , 3.40 (bs , 1 H) 131(d,J=1.42 Hz, 3H) 1.29(d,J=1.38 Hz , 3H) , 1.27 (d,J=3.92 Hz , 3H) , 1.25(d,J=3.88 Hz, 3H) . Analysis calculated for the formula $C_{11}H_{17}NO_5S$: C,47.98%; H,6.23%; N,5.09%. Actual results: C, 48.19%; H, 6.14%; N, 4.90%.

EXAMPLE 20

Reaction of (−)-diisopropyl tartrate 2,3-cyclic sulfate with $PhCO_2NH_4$

Following the general procedure described in Example 17, a solution of the cyclic sulfate (o.30 g, 1.0 mmol), and $PhCO_2NH_4$ (280 mg, 2.0 mmol) in acetone (5 ml) was stirred at 0° C. to room temperature for 4 hours. After the solvent (acetone) was evaporated, the residue was hydrolyzed with $H_2SO_4$ (20%, 10 ml) in ether for 6 hours at room temperature. After extraction and washing (excess of benzoic acid was washed out with 5% NaOH solution) the crude product was purified on silica gel (20% EtOAc in hexane) to give diisopropyl (2R,3S)-2-hydroxy-3-benzoxylsuccinate as a colorless oil in a yield of 95% (320 mg, 95%). The product had the following properties: optical rotation $[\alpha]^{23}D$ +17.43° (c 1.83, $CHCl_3$); IR (film):3480, 2980, 2930, 2880, 1730, 1600, 1580, 1465, 1450, 1370, 1275, 1235, 1180, 1100, 1025, 1000, 960, 920, 905, 820, 785, 710, 660 cm$^{-1}$; $^1$HNMR ($CDCl_3$) 8.04(dd,J=1.34, 7.31 Hz; 2H),7.54(t,J=7.23, 1H),7.44(t,J=7.90 Hz,2H),5.69 (d,J=2.40 Hz,1H),5.10–5.25(m,1H),5.05–5.15 (m,1H),4.69(dd,J=2.4,5.7 Hz,1H),3.31(d,J=5.70 Hz,1H), 1.31(d,J=3.93 Hz,3H),1.28(d,J=4.0 Hz,3H),1.26(d,J=6.04 Hz,3H),1.24(d,J=5.65 Hz,3H). Analysis calculated for the formula $C_{17}H_{22}O_7$: C, 60.34%; H, 6.56% . Actual results: C, 60.41%; H, 6.48%.

EXAMPLE 21

Reaction of (−)-diisopropyl tartrate 2,3-cyclic sulphate with nBu$_4$NNO$_3$ and NH$_4$NO$_3$ Following the general procedure described in Example 17, a solution of the cyclic sulfate (0.30 g, 1.0 mmol), NH$_4$NO$_3$ (80 mg, 1.0 mmol) and Bu$_4$NNO$_3$ in acetone (5 ml) was stirred at 0° C. to room temperature for 12 hours. After the solvent (acetone) was evaporated, the residue was hydrolyzed with H$_2$SO$_4$ (20% aqueous, 10 ml) in ether for 12 hours at room temperature. After extraction and washing the crude product was purified on silica gel (20% EtOAc in hexane) to give diisopropyl (2R,3S)-2-hydroxy-3-nitrato succinate as a colorless oil in a yield of over 90% (260 mg, 93%). The product had the following properties: $[\alpha]^{23}$D −22.98±(2.42,CHCl$_3$); IR(film):3500, 3000, 2950, 1744, 1650, 1475, 1380, 1300, 1250, 1100, 875 cm$^{-1}$; $^1$HNMR(CDCl$_3$) δ 5.56(d,J=2.35 Hz, 1H), 5.11–5.20(m,2H),4.63 (dd,J=2.4, 4.92 Hz,1H),3.30(d,J=4.92 Hz,1H),1.24–1.33 (m,12H). Analysis calculated for the formula C$_{10}$H$_{17}$NO$_8$: C,43.01%; H,6.14%; N,5.01%. Actual results: C,43.29%; H,5.91%; N,4.75%.

EXAMPLE 22

Reaction of (−)-diisopropyl tartrate 2,3-cyclic sulfate with Et$_4$NF.2H$_2$O

Following the general procedure described in Example 17, a solution of the cyclic sulfate (0.30 g, 1.0 mmol) and Et$_4$NF.2H$_2$O in acetone (5 ml) was stirred at room temperature for 5 hours. After the solvent (acetone) was evaporated, the residue was hydrolyzed with H$_2$SO$_4$ (20%, 10 ml) in ether for 12 hours at room temperature. After extraction and washing the crude product was purified on silica gel (20% EtOAc in hexane) to give diisopropyl (2R,3)-2-hydroxy-3-fluorosuccinate as a colorless oil in a yield of 90% (212 mg, 90%). The product had the following properties: optical rotation $[\alpha]^{23}$D −12.32° (C2.11,CHCl$_3$); IR(film):3500, 2980, 2930, 1740, 1460, 1370, 1280, 1250, 1210, 1180, 1100, 1020, 960, 915, 880, 830, 820, 785, 690, 660 cm$^{-1}$; $^1$HNMR(CDCl$_3$) δ 5.25,5.06(dd,J=1.84, J$_{H-F}$=71.28 Hz,1H),5.08–5.19 (m,2H),4.66,4.56(ddd,J=1.86, 5.49, J$_{H-F}$=23.77 Hz, 1H),3.28(d,J=5.48 Hz,1H),1.28(d,J=1.04 Hz,6H), 1.27(d, J=6.21 Hz,6H). Analysis calculated for the formula C$_{10}$H$_{17}$FO$_5$:C,50.84%; H,7.26%; F, 8.04%. Actual result: C,51.06%; H,7.44%; F,8.17%.

EXAMPLE 23

Reaction of (−)-diisopropyl tartrate 2,3-cyclic sulfate with benzyl magnesium chloride Benzyl magnesium chloride (0.75 ml, 1.5 mmol, 2.0 M in THF) was added dropwise to a solution of the cyclic sulfate (o.30 g, 1.0 mmol) in 10 ml of THF in the presence of Li$_2$CuCl$_4$ (0.1 ml, 0.01 mmol, 0.1 M in THF) at −75° C. The resulting orange solution was stirred from −75° C. to room temperature over a period of 2.5 hours and hydrolyzed with 20% H$_2$SO$_4$ (10 ml) in the presence of 5 ml of ether for 12 hours at room temperature. The aqueous phase was separated and extracted with ether (2×50 ml), and the combined ether layers were washed with H$_2$O, saturated NH$_4$Cl and dried over MgSO$_4$. After concentration, the crude product was purified on silica gel (20% EtOAc in hexane) to give diisopropyl (2R,3S)-2-hydroxy-3-benzylsuccinate as a pale yellow oil in a yield of 65% (200 mg, 65%). The product had the following properties: $[\alpha]^{23}$D −8.95° (c2.09,CHCl$_3$); IR(film): 3500,3060,3020,2970,2930,1720,1600,1490,1460,1450, 1370,1200,1180,1100,960,860,820,750,700,665 cm$^{-1}$; $^1$HNMR(CDCl$_3$) δ7.17–7.32 (m,5H),4.92–5.08(m,2H), 4.03(dd,J=2.65,7.11 Hz,1H),3.22(d,J=7.29 Hz,1H), 2.91–3.20(m,3H),1.24(d,J=6.03 Hz,3H),1.22(d,J=5.95 Hz, 3H),1.17(d,J=6.21 Hz,3H),1.13(d,J=6.23 Hz,3H). Analysis calculated for the formula C$_{17}$H$_{24}$O$_5$: C,66.21%; H,7.84%. Actual result: C,65.19%; H,7.67%.

EXAMPLE 24

Reaction of (−)-diethyl tartrate 2,3-cyclic sulfate with benzyl magnesium chloride Benzyl magnesium chloride (1.0 ml, 2.0 mmol, 2.0 M in THF) was added dropwise to a solution of the cyclic sulfate (0.27 g, 1.0 mmol) in 5 ml of THF and 5 ml of DME in the presence of Li$_2$CuCl$_4$ (1 ml, 0.1 mmol, 0.1 M in THF) at −78° C. The resulting orange solution was stirred from −78° C. to −20° C. over a period of 5 hours and hydrolyzed with 20% H$_2$SO$_4$(10 ml) in the presence of 5 ml of ether for 12 hours at room temperature. After workup as described above, the crude product was purified on silica gel (30% EtOAc in hexane) to give diethyl (2R,3S)-2-hydroxy-3-benzylsuccinate as a pale yellow oil in a yield of 50%. (140 mg,50%)The product had the following properties: optical rotation $[\alpha]^{23}$D −13.46° (cl.79,CHCl$_3$); IR(film): 3498,3084,3062,3027,2981,2936,1732,1603,1496,1454, 1372,1201,1111,1031,859,752,701 cm$^{-1}$; $^1$HNMR(CDCl$_3$) δ7.15–7.35 (m,5H),4.05–4.3(m,5H), 3.1–3.25(m,3H ),3.0(m,1H), 1.15–1.30(m,6H).

EXAMPLE 25

Reaction of (−)-dimethyl tartrate 2,3-cyclic sulfate with benzyl magnesium chloride Benzyl magnesium chloride (1.0 ml, 2.0 mmol, 2.0 M in THF) was added dropwise to a solution of the cyclic sulfate 0.24 g, 1.0 mmol) in 5 ml of THF and 5 ml of DME in the presence of Li$_2$CuCl$_4$ (1 ml, 0.1 mmol , 0.1 M in THF) at =78 ° C. The resulting orange solution was stirred from =78° C. to −20° C. a period of 5 hours and hydrolyzed with 20% H$_2$SO$_4$ (10 ml) in the presence of 5 ml of ether for 12 hours at room temperature. After workup as described above, the crude product was purified on silica gel (30% EtOAc in hexane) to give dimethyl (2R,3S)-2-hydroxy-3-benzylsuccinate as a pale yellow oil in a yield of more than 30% (80 mg,33%). The product had the following properties:- $[\alpha]^{23}$D −21.45° (cl.10,CHCl$_3$); IR(film): 3489,3061,3027,2952,1745,1603,1496,1454,1438, 1216,1112,1028, 835,752,701 cm$^{-1}$; $^1$HNMR(CDCl$_3$) δ 7.15–7.4(m,5H),4.07(dd,J=2.74,7.17 Hz,1H), 3.74(s,3H),3.66(s,3H),3.15–3.25(m,3H), 2.97(dd,J=11.63, 15.12 Hz,1H).

EXAMPLE 26

Reaction of (−)-diethyl tartrate 2,3-cyclic sulfate with NaN$_3$

NaN$_3$ (0.20 g, 3.0 mmol) was added to a cooled (ice water) solution of (-)-diethyl tartrate 2,3-cyclic sulfate (0.54 g, 2.0 mmol) in 5 ml of H$_2$O and 5 ml of acetone, and the solution was stirred room temperature for 1.5 hours. After evaporation of acetone, the solution was hydrolyzed with 20% H$_2$SO$_4$ (10 ml) in presence of 10 ml of ether for 10 hours. After usual workup, the crude product was purified on silica gel (30% EtOAc in hexane) to give diethyl (2S,3R(-2-azido-3-hydroxysuccinate as a colorless liquid in a yield of over 80%(0.38 g,, 82.2%). The product had the following properties: optical rotation $[\alpha]^{23}D$ +8.24° (c1.88,$CH_2Cl_2$),(lit. $[\alpha]^{18}D$ +16.5° (1.47,$CH_2Cl_2$)); IR(film):3483,2978, 2120,1742, 1467,1443,1367,1208,1108, 1020,855 $cm^{-1}$; $^1HNMR(CDCl_3)$ $\delta$ 4.60(dd,J=2.67,5.45 Hz,1H), 4.22–4.35(m,5H),3.26(d,J=5.36 Hz,1H),1.26–1.32(m,6H); $^{13}CNMR(CDCl_3)$ 170.71,166.92, 72.07,64.46,62.61,62.27, 13.96; Analysis calculated for the formula $C_8H_{13}N_3O_5$: C,41.56%; H,5.67%; N,18.17%. Actual result: C,41.70%; H,5.67%; N,18.20%.

EXAMPLE 27

Catalytic reduction of diethyl (2S,3R)-2-azido-34-hydroxy succinate

A solution of diethyl (2S,3R)-2-azido3-hydroxysuccinate (114 mg, 0.5 mmol) in 2 ml of EtOAc in the presence of catalytic amount of 10% Pd on carbon (10% by weight) was stirred under about 1 atm of hydrogen for about 12 hours at room temperature. The mixture was then filtered through a pad of Celite and concentrated to give about 85 mg of diethyl L-erythro-$\beta$-hydroxyaspartate as an oil. This compound was used without further purification.

EXAMPLE 28

Diethyl N-(tert-Butoxycarbonyl)-L-erythro-$\beta$-hydroxyaspartate

A solution of diethyl L-erythro-$\beta$-hydroxyaspartate (80 mg, 0.39 mmol) and di-tert-butyl dicarbonate (0.11 mL, 0.47 mmol) in 2 ml of $CHCl_3$ was stirred at room temperature for 2 hours. The mixture was then concentrated, and the residue was purified on silica gel to give diethyl N-(tert-butoxycarbonyl)-L-erythro-$\beta$ hydroxyaspartate as a colorless oil in a yield of about 88% (105 mg, 88.2%). The product had the following properties:- $[\alpha]^{23}D$+17.0° c4.42,$CH_2Cl_2$),(lit.$[\alpha]^{21}D$+22.5° [1.19,$CH_2Cl_2$]); IR(film): 3445,2981,1716,1504,1369, 1163,1118, 1059,1027, 864 $cm^{-1}$; $HNMR(CDCl_3)$ $\delta$ 5.52(d,J=7.91 Hz,1(m,4H), 3.50(d,J=5.12 Hz,1H), 1.41(s,9H),1.28(t,J=7.22 Hz,3H), 1.20(t,J=7.20 Hz,3H); $^{13}C$ NMR $(CDCl_3)$ $\delta$ 171.5,168.5,155.6,80.4,72.1,62.1,61.9,57.0, 28.2,14.0,13.9. Analysis calculated for the formula $c_{13}H_{23}NO_7$: C,51.14%; H,7.59%; N,4.59%. Actual result: C,51.34%; H,7.35%; N,4.43%.

EXAMPLE 29

Reduction of (−)-diisopropyl tartrate cyclic sulfate with $NaCNBH_3$ $NaCNBH_3$(0.126 g, 2.0 mmol) was added to a solution of (−) -diisopropyl tartrate cyclic sulfate (0.30 g, 1 . 0 retool) in 5 ml of THF in the presence of a trace amount of bromocresol green (pH 3.8–5.4) at room temperature . After addition, the solution turned green . 1 N HCl in methanol was added until the color became greenish yellow and the solution was heated at about 65° C. During the reaction, 1 N HCl in methanol was added to maintain the greenish yellow color. After about 3 hours , color fainted and a white suspension was formed which was heated for 2 hours until no starting material was left. The mixture was then cooled to room temperature and stirred with 5 ml of 20% $H_2SO_4$ in the presence of 10 ml of ether for about 12 hours. The solution was then diluted with 150 ml of ether and the aqueous phase was separated. The organic phase was washed with $H_2O$ (10 ml), brine (10 ml) and dried over $MgSO_4$. After concentration, the crude product was purified on silica gel (20% EtOAc in hexane) to give (R)-D-diisopropyl malate as a colorless oil in a yield of 55% (0.120 g, 55%). The product had the following properties: optical rotation $[\alpha]^{23}D$+10.77° (c2.47,$CHCl_3$); IR(film):3493,2981, 2937,1736,1468,1375,1272,1181,1146,1105,960,824,736 $cm^{-1}$; $^1HNMR(CDCl_3)$ $\delta$ 4.99–5.15(m,2H),4.42(dt,J=5.41,5.04 Hz , 1H) , 3.20(d,J=5.41 Hz,1H) ,2.80(dd, J=3.98,15.6 Hz,1H) ,2.72 (dd,J=5.70,15.6 Hz,1H) ,1.21–1.28 (m,12H). Analysis calculated for the formula $C_{10}H_{18}O_5$: C,55.03%; H,8.31%.Actual result: C,55.15; H,8.30.

EXAMPLE 30

Preparation of N- substituted Aziridines From Cyclic Sulfates

To a solution of 1-(R)-cyclohexyl-1,2-cyclic sulfate (1.03 g, 5 mmol) in dry THF (50 mL) was added benzylamine (1.07 g, 10 mmol). After refluxing for 8 hours at ca. 60° C. (TLC reveals disappearance of the cyclic sulfate), the reaction mixture was cooled to room temperature and n-BuLi (6 mL, 12 mmol, 2M in hexane) was slowly added. The resulting pale yellow solution was stirred at room temperature for 2 hours and then diluted with ether (50 mL), washed with water (2×20 mL), brine (20 mL) and dried over $Na_2SO_4$. Removal of the solvent gave 2(S)-cyclohexyl-l-benzylaziridine (0.837 g, 78%) as a pale yellow oil. Alternatively, after refluxing a mixture of 1-(R)-cyclohexyl-1,2-cyclic sulfate (1.03 g, 5 mmol) and benzylamine (1.07 g, 10 mmol) n dry THF (50 mL) for 8 hours, the reaction mixture was cooled to room temperature and $LiAlH_4$(0.28 g, 7.5 mmol) was added slowly and the reaction mixture was further refluxed for 8 hours. Excess LiAlH is quenched with 20% aq. KOH (ca 2–3 mL). The reaction mixture was filtered and the filtrand was washed with hot THF (3×20–30 mL). The combined filtrates were concentrated under reduced pressure and the residual oil is dissolved in ether (50 mL) and washed with water (20 mL), brine (20 mL) and dried over $Na_2SO_4$. Removal of the solvent gave almost pure 2(S)-cyclohexyl-l-benzylaziridine (0.827 g, 77%) as a pale yellow oil, $^1H$ NMR (CDClhd 3 $\delta$ 7.25 (m, 5 H), 3.45 (d,J=12 Hz, 1 H), 3.18 (d, J=12 Hz, 1 H), 1.7–0.8 (br m, 4 H). The product could be further purified by chromatography on silica gel.

EXAMPLE 31

Preparation of N-substituted Amino Alcohols

Following removal of the solvent under reduced pressure, the $\beta$-aminosulfate from the reaction of 1-(R)-cyclohexyl-l,2-cyclic sulfate (0.206 g, 1 mmol) and benzylamine (0.214 g, 2 mmol) was stirred with 20% $H_2SO_4$ (5 mL) and ether (5 mL) at room temperature (refluxing of the two phase mixture expedites the hydrolysis) for 12 hours. The organic phase was discarded and the aqueous phase was adjusted to pH 10 with 20% aq. NaOH and extracted with ether (3×20 mL). The combined organic phases were washed with brine (20 mL) and dried over $Na_2SO_4$. Concentration gave 1(R)- cyclohexyl-2-benzylaminoethanol (0.117 g, 74%), mp. 56°–58° C., $[\alpha]^{22}D = -1.2°$ (c 1, CHCl$_3$; $^1$H NMR (CDCl$_3$) δ 7.3 (S, 5 H), 3.75 (d, J 5.77 Hz, 2 H), 3.35 (m, 1 H), 2.75 (dd, J =2.5, 9.6 Hz, 2 H), 2.5 (dd, J 9.6, 13 Hz, 1 H), 1.9–1.5 (m, 5 H), 1.3–0.9 (m, 7 H).

EXAMPLE 32

Preparation of N-Unsubstituted Aziridines

To a solution of 1-(R)-cyclohexyl-1,2-cyclic sulfate (0.412 g, 2 mmol) in dry THF (20 mL) was added LiN$_3$ (0.196 g, 4 mmol, 2 eq.) and the reaction mixture was refluxed for 12 hours during which time all the cyclic sulfate was consumed (TLC). The reaction mixture was cooled to room temperature and LiAlH$_4$ (0.11 g, 3 mmol, 1.5 eq.) was added slowly and then the reaction mixture was refluxed for another 8 hours. Solvent was removed under vacuum and excess LiAlH$_4$ was carefully quenched with 20% aq. KOH (5 mL). The reaction mixture was diluted with water (30 mL) and the aziridine was distilled with water at atmospheric pressure. The distillate was extracted with ether (3×20 mL) and the combined extracts washed with brine (10 mL) and dried over Na$_2$SO$_4$. Removal of the solvent gave 2-(S)-cyclohexylaziridine as an oil in good yield (0.20 g, 80%) having the following properties: $^1$H NMR (CDCl$_3$) δ 1.0 (br d, J 9 Hz, 1 H), 1.7 (br m, 6 H), 1.35 (m, 1 H), 1.1 (m, 6 H), 0.8 (br s, 1 H).

EXAMPLE 33

Preparation of D-Mannitol 1,2:5,6-diacetonide, 2,3-Cyclic Sulfate

To a cooled (ice-water), magnetically stirred solution of 1,2:5,6-diisopropylidene D-mannitol (5.35 g, 20.0 mmol) and triethylamine (11.15 mL, 8.095 g, 80.0 mmol) in dichloromethane (60 mL) was added a dichloromethane solution (5 mL) of thionyl chloride (2.18 mL, 3,569 g, 30.0 mmol) dropwise over a period of 10 minutes. Stirring was continued for 5 minutes at 0° C. (the reaction was followed by TLC). The reaction mixture was diluted with cold ether (100 mL) and washed with cold water (2×100 mL) and brine (100 mL). The organic solution was dried over MgSO$_4$ and filtered. The filtrate was concentrated by rotary evaporation, the residue was pumped under reduced pressure (0.2 mm Hg, 1 h), and to this residue was added a cold solution of CCl$_4$ (60 mL) and CH$_3$CN (60 mL). The flask was cooled in an ice bath and cold water (90 mL) was added. RuCl$_3$.H$_2$O (23 mg, 0.1 mmol) and NaIO$_4$ (8.56 g, 40.0 mmol) were added at once and the reaction mixture was stirred vigorously at 0° C. The reaction was followed by TLC. After 45 minutes of stirring, ether (120 mL) was added and the layers were separated. The aqueous layer was extracted with ether (50 mL) and the combined organic layers were washed with brine (60 mL). Drying (MgSO$_4$), followed by concentration of the filtrate, furnished 6.46 g of a pale yellow solid. This crude product was recrystallized in a minimum amount of acetone (10 mL) and petroleum ether (35°–60° C., 150 mL) to yield 5.59 g as a first crop and 0.55 g from the mother liquor (overall 94% yield) having the following properties: $[\alpha]23D +28.7$ (c 2.9, CHCl$_3$), mp 124.0°–126.0° C. (118.5° C. deform). IR (cm$^{-1}$, KBr) 2993, 2937, 2907, 1560, 1457, 1396, 1372, 1260, 1241, 1208, 1146, 1080, 1055, 952, 914, 830, 786, 670, 644. $^1$H NMR(CDCl$_3$) 1.35 (6H, s), 1.45 (6H, s), 4.06 (2H, ABX, $J_{AB}$=9.6 Hz, $J_{AX}$3.5 Hz), 4.19 (2H, ABX, $J_{AB}$−9.6 Hz, $J_{BX}$=6.1 Hz, 4.45 (2H, m), 4.68–4.72 (2H, m). $^{13}$CNMR (CDCl$_3$) 24.79, 26.65, 66.16, 73.50, 82.48, 110.99. Anal. Calcd for C$_{12}$H$_{20}$O$_8$S: C, 44,43; H, 6.22; S, 9.87. Found: C, 44.07; H, 6.10; S, 9.83.

EXAMPLE 34

Preparation of 3-Azido-3-Deoxy-1,2:5,6-di-O-Isopropylidene-D-Altritol

A mixture of D-mannitol 1,2:5,6-diacetonide 2,3-cyclic sulfate (163 mg, 0.500 mmol) and LiN$_3$ (49 mg, 1.00 mmol) in dry DMF (2.5 mL) was stirred under nitrogen for 3 hours at 70°–80° C. The solvent was then removed under reduced pressure (0.2 mm Hg, T$_b$ 40° C.). The residue was suspended in dry THF (5 mL), and concd H$_2$SO$_4$ (25 μL) and water (9 μL) were added to the stirred suspension. The hydrolysis was followed by TLC (Hex-EtOAc=2:1). After 20 minute excess sodium bicarbonate (100 mg) was added and the reaction mixture was stirred for 20 minutes. Filtration through a Gelire and silica gel bed and concentration of the filtrate under reduced pressure provided a viscous, pale yellow oil. Column chromatography (silica gel, Hex-EtOAc=5:1 v/v) of the crude produce gave 131 mg (91% yield) of 3-azido-3-deoxy-1,2:5,6-di-O-isopropylidene-D-altritol as a colorless oil having the following properties: IR (cm$^{-1}$, film) 3454(br), 2987, 2963, 2936, 2111, 1456, 1372, 1215, 1179, 1157, 1062. $^1$H NMR (CDCl$_3$) 1.34 (3H, s), 1.37(3H,s), 1.40 (3H, s), 1.48 (3H, s), 2.82 (—OH, d, J=6.2 Hz), 3.32 (1H, t, J=5.3 Hz), 3.77–4.21 (6H, m), 4.47 (1H, dt, J=5.1, 6.5 Hz). $^{13}$C NMR (CDCl$_3$13 25.13, 25.23, 26.15, 26.53, 63.43, 66.04, 66.65, 72.54, 75.82, 76.04, 109.57, 109.97. Anal. Calcd for C$_{12}$H$_{21}$N$_3$O$_5$: C, 50.15; H, 7.37; N, 14.63. Found: C, 50.26; H, 7.15; N, 14.42.

EXAMPLE 35

Preparation of 2-octyl-cyclopropane-1,1-dimethylcarboxylate

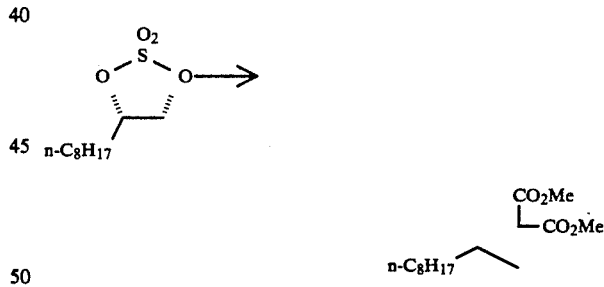

NaH (150 mg, 6.2 mmol) was added to a solution of dimethyl malonate (400 mg, 3.0 mmol) in 7 mL of dimethoxy ethane (DME) at 0° C. The resulting mixture was stirred at room temperature for ca. 15 min. 1,2-Decanediol cyclic sulfate (473 mg, 2.0 mmol) in 3 mL of DME was then added, and the resulting mixture was heated at ca. 85° C. for 42 h. After the mixture was cooled, it was diluted with ether and washed with water, brine, and dried over MgSO$_4$. The crude product was purified by chromatography (20% EtOAc in hexane) to afford 2-octyl-cyclopropane-1,1-dimethylcarboxylate as a colorless oil (390 mg, 72%): IR (film) 2960, 2940, 2860, 1730, 1440, 1330, 1290, 1215, 1135, 1000 cm$^{-1}$; $^1$H NMR (CDCl$_3$) δ 3.76 (s, 3 H), 3.72 (s, 3H), 1.8–2.0 (m, 1 H), 1.1–1.5 (m, 16 H), 0.90 (t, J=6.3 Hz, 3 H). Anal. Calcd for C$_{15}$H$_{26}$O$_4$: C, 66.63; H, 9.69. Found: C, 66.89; H, 9.70.

Equivalents

Those skilled in the art will recognize, or be able to ascertain, using no more than routine experimentation, numerous equivalents to the specific substances and procedures described herein. Such equivalents are considered to be within the scope of this invention, and are covered by the following claims.

We claim:

1. A method of producing a compound of the general formula:

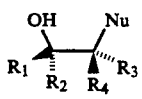

wherein the Nu represents a selected nucleophile and $R_1$, $R_2$, $R_3$ and $R_4$ are selected from the group consisting of hydrogen, alkyl groups, aryl groups, carbonyl groups, carboxylic groups, carboxyalkyl groups and amide groups, comprising the steps of:
   a) combining a selected vicinal dihydroxy compound and a thionyl halide under conditions appropriate for reaction of the vicinal dihydroxy compound with the thionyl halide to occur;
   b) adding to the combination formed in step (a) a catalytic amount of from about 0.001 to about 0.02 equivalents of a ruthenium-containing compound, and a periodate, under conditions appropriate for oxidation of the product of the reaction in step (a) to occur, to produce the cyclic sulfate; and
   c) combining the cyclic sulfate and the selected nucleophile, under conditions appropriate for reaction of the cyclic sulfate and the nucleophile to occur.

2. A method of claim 1 wherein the starting compound is a tartrate diester.

3. A method of producing a compound of the general formula:

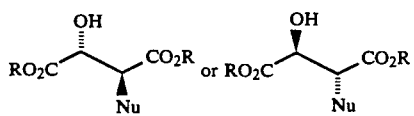

wherein R represents an alkyl or cycloalkyl group and Nu represents a selected nucleophile, comprising the reaction of a tartrate cyclic sulfate with a nucleophile in a suitable solvent or a solvent mixture under conditions appropriate for the reaction to occur.

4. A method of claim 3 wherein the tartrate cyclic sulfate is formed from a L-tartrate diester starting compound.

5. A method of claim 3 wherein the tartrate cyclic sulfate is formed from a D-tartrate diester starting compound.

6. A method of claim 3 wherein the nucleophile is chosen from the group consisting of alkylmagnesium halides (Grignard reagents), alkali metal azides, ammonium thiocyanate, tetraalkylammonium nitrate, ammonium nitrate, ammonium hydrogen fluoride, tetraethylammonium fluoride, ammonium benzoic acid salt, and sodium cyanoborohydride.

7. A method of producing a disubstituted compound of the general formula:

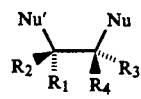

wherein Nu and Nu' represent selected nucleophiles, and $R_1$, $R_2$, $R_3$ and $R_4$ are selected from the group consisting of hydrogen, alkyl groups, aryl groups, carbonyl groups, carboxylic acids, carboxyalkyl groups and amide groups, comprising the steps of:
   a) combining a selected vicinal dihydroxy compound and a thionyl halide under conditions appropriate for reaction of the vicinal dihydroxy compound with the thionyl halide to occur;
   b) adding to the combination formed in step a) catalytic amount of from about 0,001 to about 0.02 equivalents of a ruthenium-containing compound, and a periodate, under conditions appropriate for oxidation of the product of the reaction in step a) to occur to produce a cyclic sulfate;
   c) combining the cyclic sulfate and the selected nucleophile, Nu, under conditions appropriate for reaction of the cyclic sulfate and Nu to occur, thereby forming a monosubstituted compound having the general formula:

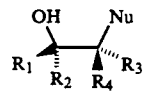

d) combining the monosubstituted compound of step c) with a hydroxyl-activating agent under conditions appropriate for activation of the hydroxyl groups to occur; and
   e) adding the selected nucleophile, Nu', under conditions appropriate for reaction of the monosubstituted compound of step c) and Nu' to occur, thereby forming said disubstituted compound.

* * * * *